United States Patent
Jegla et al.

(10) Patent No.: US 6,586,179 B1
(45) Date of Patent: Jul. 1, 2003

(54) HUMAN EAG2

(75) Inventors: Timothy J. Jegla, Durham, NC (US); Yi Liu, Cary, NC (US)

(73) Assignee: ICAgen, Incorporated, Durham, NC (US)

(*) Notice: Subject to any disclaimer, the term of this patent is extended or adjusted under 35 U.S.C. 154(b) by 0 days.

(21) Appl. No.: 09/614,480

(22) Filed: Jul. 10, 2000

Related U.S. Application Data

(60) Provisional application No. 60/143,467, filed on Jul. 13, 1999.

(51) Int. Cl.[7] .......................... C12Q 1/68; C07H 17/00; C12P 21/06; C07K 14/00
(52) U.S. Cl. .......................... 435/6; 536/23.1; 435/69.1; 435/325; 435/320.1; 435/252.3; 530/350
(58) Field of Search .......................... 536/23.1; 435/7.1, 435/325, 320.1, 252.3; 530/350; 436/6

(56) References Cited

PUBLICATIONS

Ludwig et al. 1994; EMBO J. 13: 4451–4458.*
Volario et al. 1998; DNA Seq. 9(5–6):307–315.*
Bruggemann, Andrea et al., "Ether–à–go–go encodes a voltage–gated channel permeable to $K^+$ and $Ca^{2+}$ and modulated by cAMP," Nature 365:445–448 (Sep. 1993).
Frings, Stephan et al., "Characterization of Ether–à–go–go Channels Present in Photoreceptors Reveals Similarity to $I_{KX}$, a $K^+$ Current in Rod Inner Segments," J. Gen. Physiol. 111:583–599 (Apr. 1998).
Occhiodoro, Teresa et al., "Cloning of a human ether–a––go–go potassium channel expressed in myoblasts at the onset of fusion," Federation of European Biochemical Societies 434:177–182 (1998).
Robertson, G. A. et al., "Potassium Currents Expressed from Drosophila and Mouse eag cDNAs in Xenopus Oocytes," Neuropharmacology 35(7):841–850 (1996).
Shi, Wenmei et al., "Cloning of a mammalian elk potassium channel gene and EAG mRNA distribution in rat sympathetic ganglia," Journal of Physiology 511(3):675–682 (1998).
Warmke, Jeffrey et al., "A Distinct Potassium Channel Polypeptide Encoded by the Drosophila eag Locus," Science 252:1560–1562 (1991).
Saganich et al., "Cloning of Components of a Novel Subthreshold–Activating $K^+$ Channel With a Unique Pattern of Expression in the Cerebral Cortex," J. Neuroscience, vol. 19, No. 24, pp. 10789–10802 (1999).

* cited by examiner

*Primary Examiner*—Karen Cochrane Carlson
(74) *Attorney, Agent, or Firm*—Townsend and Townsend and Crew LLP

(57) ABSTRACT

The invention provides isolated nucleic acid and amino acid sequences of Eag2, antibodies to Eag2, methods of detecting Eag2, and methods of screening for modulators of Eag2 potassium channels using biologically active Eag2. The invention further provides, in a computer system, a method of screening for mutations of human Eag2 genes as well as a method for identifying a three-dimensional structure of Eag2 polypeptide monomers.

12 Claims, 4 Drawing Sheets

```
  1    M--PGGKRGLVAPQNTFLENIVRRSSESSFLLGNAQIVDWPVVYSNDGFCKLSGYHRADV      hEag2.PRO
  1    MTMAGGRRGLVAPQNTFLENIVRRSNDTNEVLGNAQIVDWPIVYSNDGFCKLSGYHRAEV      hEag1.PRO

59    MQKSSTCSFMYGELTDKKTIEKVRQTEDNYESNCPEVLLYKKNRTPVWFYMQIAPIRNEH      hEag2.PRO
 61    MQKSSTCSFMYGELTDKDTIEKVRQTFENYEMNSPEILMYKKNRTPVWFFVKLAPIRNEQ      hEag1.PRO

119    EKVVLFLCTFKDITLFKQPIEDDSTKGWTKFARLTRALTNSRSVLQQITP-MNKTEVVHK      hEag2.PRO
121    DKVVLFLCTFSDITAEKQPIEDDSCKGWGKFARLTRALTSSRGVLQQLAPSVQKGENVHK      hEag1.PRO

178    HSRLAEVLQLGSDILPQYKQEAPKTPPHIILHYCAFKTTWDWVILILTFYTAMVPYNVS      hEag2.PRO
181    HSRLAEVLQLGSDILPQYKQEAPKTPPHIILHYCVFKTTWDWIILILTFYTALVPYNVS      hEag1.PRO

238    FKTRQNNIAWLVLDSVVDVIFLVDIVLNFHTTFVGPGEVISDPKLIRMNYLKTWFVIDL      hEag2.PRO
241    FKTRQNNVAWLVVDSIVDVIFLVDIVLNFHTTFVGPAGEVISDPKLIRMNYLKTWFVIDL      hEag1.PRO

298    LSCLPYDIINAFENVDEGISSLFSSLKVVRLLRLGRVARKLDHYLEYGAAVLVLLVCVFG      hEag2.PRO
301    LSCLPYDVINAFENVDEGISSLFSSLKVVRLLRLGRVARKLDHYIEYGAAVLVLLVCVFG      hEag1.PRO

358    IVAHWLACIWYSIGDYEVIDEVNTIQIDSWLYQLALSIGTPYRYNTSA-GIWEGGPSRD      hEag2.PRO
361    LAAHWMACIWYSIGDYEIFDEDTKIRNNSWLYQLAMDIGTPYQFNGSGKWEGGPSKN      hEag1.PRO

417    SLYVSSLYFTMTSLTTIGFGNIAPTTDVEKMFSVAMMVGSLLYATIFGNVTTIFQQMYA      hEag2.PRO
421    SVYISSLYFTMTSLTSVGFGNIAPSTDIEKIEAVAIMMIGSLLYATIFGNVTTIFQQMYA      hEag1.PRO

477    NTNRYHEMLNNVRDFLKLYQVPKGLSERVMDYIVSTWSMSKGIDTEKVLSICPKDMRADI      hEag2.PRO
481    NTNRYHEMLNSVRDFLKLYQVPKGLSERVMDYIVSTWSMSRGIDTEKVLQICPKDMRADI      hEag1.PRO

537    CVHLNRKVEHPAFRLASDGCLRALAVEFQTIHCAPGDLIYHAGESVDALCFVVSGSLE      hEag2.PRO
541    CVHLNRKVEHPAFRLASDGCLRALAMEFQTVHCAPGDLIYHAGESVDSLCFVVSGSLE      hEag1.PRO
```

FIG. 1A.

```
597 VIQDDEVVAILGKGDVFGDIFWKETTLAHACANVRALTYCDLHITKREALLKVLIDFYTAF  hEag2.PRO
601 VIQDDEVVAILGKGDVFGDVFWKEATLAQSCANVRALTYCDLHVIKRDALQKVLEFYTAF  hEag1.PRO

657 ANSFSFNLTLTCNLRKRIIFRKISDVKKEEEERLRQKNEVTLSIPVDHPVRKLFQKFKQQ  hEag2.PRO
661 SHSFSFNLILTYNLRKRIVERKISDVKREEEERMKRKNEAPLIIPPDHPVRRLFQRFRQQ  hEag1.PRO

717 KELRNQGSTQGDPERNQLQVESRSLQNGTSITGTSVVTVSQITPIQTSLAYVKTSESLKQ  hEag2.PRO
721 KEAR-LAAERGGRDLDDLDVEKGNVLTEHASANHSLVKASVVTVRESPATPVSFQAASTS  hEag1.PRO

777 NNRDAMELKPNGGADQKCLKVNSPIRMKNGNG----KGWLRLKNNMGAHEEKKEDWNNV  hEag2.PRO
780 GVPDHAKLQAPGSE---CI---GP-KGGGGDCAKRKSWARFKDACG---KSEDWNKV  hEag1.PRO

832 TKAESMGLISEDPKSSDSENSVTKNPLRKTDSCDSGITKSDLRLDKAGEARSPLEHSPIQ  hEag2.PRO
827 SKAESMETLPERTKASGEAT-----LKKTDSCDSGITKSDLRLDNVGEARSPQDRSPIL  hEag1.PRO

892 ADAKHPFYPIPEQALQTTLQEVKHELKEDIQLISCRMTALEKQVAEILKILSEKSVPQAS  hEag2.PRO
881 AEVKHSFYPIPEQTLQATVIEVRHELKEDIKALNAKMTNIEKQLSEILRILTSRRSSQSP  hEag1.PRO

952 SPKSQMPLQVPPQIPCQDIFSVSRPESPESDKDEIHF.  hEag2.PRO
941 ------------------QELEEISRPQSPESERDIFGAS  hEag1.PRO
```

FIG. 1B.

*A.*
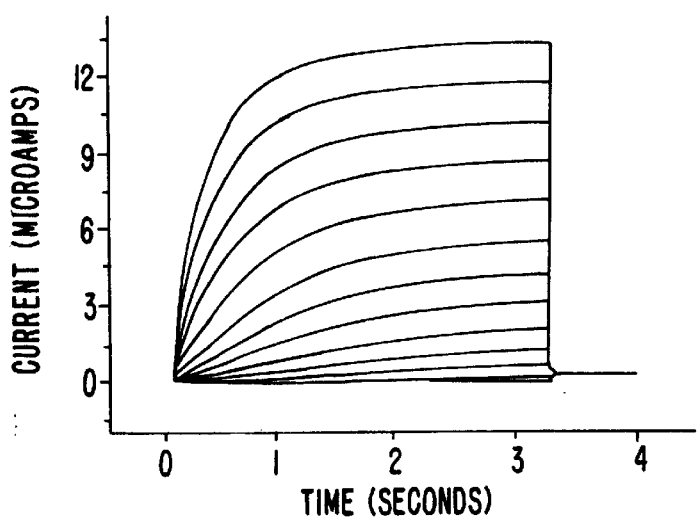
*B.*
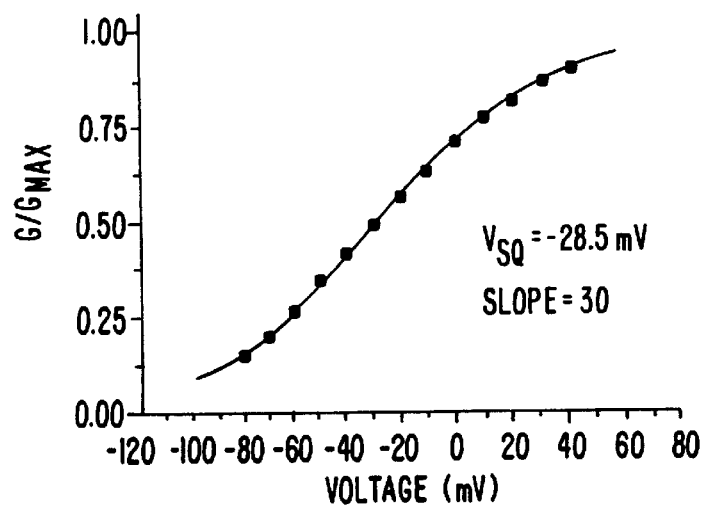
*C.*
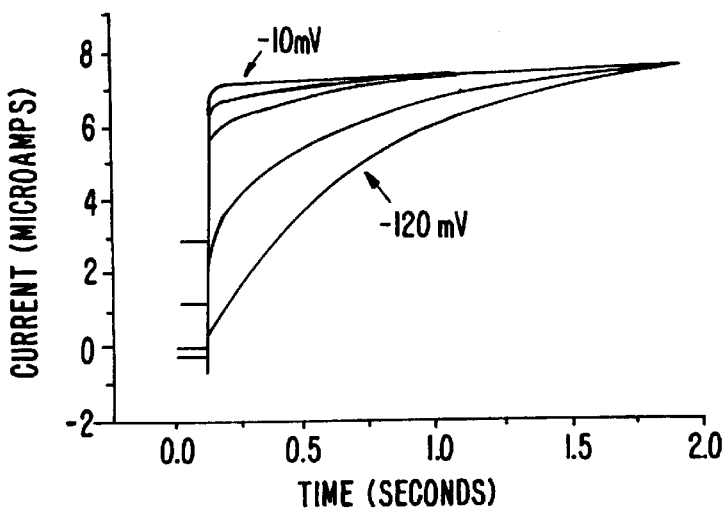
*FIG. 2.*

SEQUENCE LISTING

```
<160> NUMBER OF SEQ ID NOS: 9

<210> SEQ ID NO 1
<211> LENGTH: 2967
<212> TYPE: DNA
<213> ORGANISM: Homo sapiens
<220> FEATURE:
<221> NAME/KEY: CDS
<222> LOCATION: (1)..(2967)
<223> OTHER INFORMATION: human ether a go-go (Eag) 2 voltage-gated
      potassium channel

<400> SEQUENCE: 1
```

```
atg ccg ggg ggc aag aga ggg ctg gtg gca ccg cag aac aca ttt ttg      48
Met Pro Gly Gly Lys Arg Gly Leu Val Ala Pro Gln Asn Thr Phe Leu
 1               5                  10                  15 gag aac atc gtc agg cgc tcc agt gaa tca agt ttc tta ctg gga aat      96
Glu Asn Ile Val Arg Arg Ser Ser Glu Ser Ser Phe Leu Leu Gly Asn
                20                  25                  30 gcc cag att gtg gat tgg cct gta gtt tat agt aat gac ggt ttt tgt     144
Ala Gln Ile Val Asp Trp Pro Val Val Tyr Ser Asn Asp Gly Phe Cys
            35                  40                  45 aaa ctc tct gga tat cat cga gct gac gtc atg cag aaa agc agc act     192
Lys Leu Ser Gly Tyr His Arg Ala Asp Val Met Gln Lys Ser Ser Thr
        50                  55                  60 tgc agt ttt atg tat ggg gaa ttg act gac aag aag acc att gag aaa     240
Cys Ser Phe Met Tyr Gly Glu Leu Thr Asp Lys Lys Thr Ile Glu Lys
 65                  70                  75                  80 gtc agg caa act ttt gac aac tac gaa tca aac tgc ttt gaa gtt ctt     288
Val Arg Gln Thr Phe Asp Asn Tyr Glu Ser Asn Cys Phe Glu Val Leu
                85                  90                  95 ctg tac aag aaa aac aga acc cct gtt tgg ttt tat atg caa att gca     336
Leu Tyr Lys Lys Asn Arg Thr Pro Val Trp Phe Tyr Met Gln Ile Ala
            100                 105                 110 cca ata aga aat gaa cat gaa aag gtg gtc ttg ttc ctg tgt act ttc     384
Pro Ile Arg Asn Glu His Glu Lys Val Val Leu Phe Leu Cys Thr Phe
        115                 120                 125 aag gat att acg ttg ttc aaa cag cca ata gag gat gat tca aca aaa     432
Lys Asp Ile Thr Leu Phe Lys Gln Pro Ile Glu Asp Asp Ser Thr Lys
130                 135                 140 ggt tgg acg aaa ttt gcc cga ttg aca cgg gct ttg aca aat agc cga     480
Gly Trp Thr Lys Phe Ala Arg Leu Thr Arg Ala Leu Thr Asn Ser Arg
145                 150                 155                 160 agt gtt ttg cag cag ctc acg cca atg aat aaa aca gag gtg gtc cat     528
Ser Val Leu Gln Gln Leu Thr Pro Met Asn Lys Thr Glu Val Val His
                165                 170                 175 aaa cat tca aga cta gct gaa gtt ctt cag ctg gga tca gat atc ctt     576
Lys His Ser Arg Leu Ala Glu Val Leu Gln Leu Gly Ser Asp Ile Leu
            180                 185                 190 cct cag tat aaa caa gaa gcg cca aag acg cca cca cac att att tta     624
Pro Gln Tyr Lys Gln Glu Ala Pro Lys Thr Pro Pro His Ile Ile Leu
        195                 200                 205 cat tat tgt gct ttt aaa act act tgg gat tgg gtg att tta att ctt     672
His Tyr Cys Ala Phe Lys Thr Thr Trp Asp Trp Val Ile Leu Ile Leu
    210                 215                 220 acc ttc tac acc gcc att atg gtt cct tat aat gtt tcc ttc aaa aca     720
Thr Phe Tyr Thr Ala Ile Met Val Pro Tyr Asn Val Ser Phe Lys Thr
225                 230                 235                 240 aag cag aac aac ata gcc tgg ctg gta ctg gat agt gtg gtg gac gtt     768
Lys Gln Asn Asn Ile Ala Trp Leu Val Leu Asp Ser Val Val Asp Val
                245                 250                 255 att ttt ctg gtt gac atc gtt tta aat ttt cac acg act ttc gtg ggg     816
Ile Phe Leu Val Asp Ile Val Leu Asn Phe His Thr Thr Phe Val Gly
            260                 265                 270 ccc ggt gga gag gtc att tct gac cct aag ctc ata agg atg aac tat     864
Pro Gly Gly Glu Val Ile Ser Asp Pro Lys Leu Ile Arg Met Asn Tyr
        275                 280                 285 ctg aaa act tgg ttt gtg atc gat ctg ctg tct tgt tta cct tat gac     912
Leu Lys Thr Trp Phe Val Ile Asp Leu Leu Ser Cys Leu Pro Tyr Asp
    290                 295                 300 atc atc aat gcc ttt gaa aat gtg gat gag gga atc agc agt ctc ttc     960
Ile Ile Asn Ala Phe Glu Asn Val Asp Glu Gly Ile Ser Ser Leu Phe
305                 310                 315                 320
```

-continued

| | | |
|---|---|---|
| agt tct tta aaa gtg gtg cgt ctc tta cga ctg ggc cgt gtg gct agg<br>Ser Ser Leu Lys Val Val Arg Leu Leu Arg Leu Gly Arg Val Ala Arg<br>                  325                        330                    335 | 1008 |
| aaa ctg gac cat tac cta gaa tat gga gca gca gtc ctc gtg ctc ctg<br>Lys Leu Asp His Tyr Leu Glu Tyr Gly Ala Ala Val Leu Val Leu Leu<br>                340                       345                    350 | 1056 |
| gtg tgt gtg ttt gga ctg gtg gcc cac tgg ctg gcc tgc ata tgg tat<br>Val Cys Val Phe Gly Leu Val Ala His Trp Leu Ala Cys Ile Trp Tyr<br>        355                       360                      365 | 1104 |
| agc atc gga gac tac gag gtc att gat gaa gtc act aac acc atc caa<br>Ser Ile Gly Asp Tyr Glu Val Ile Asp Glu Val Thr Asn Thr Ile Gln<br>370                       375                       380 | 1152 |
| ata gac agt tgg ctc tac cag ctg gct ttg agc att ggg act cca tat<br>Ile Asp Ser Trp Leu Tyr Gln Leu Ala Leu Ser Ile Gly Thr Pro Tyr<br>385                       390                     395                  400 | 1200 |
| cgc tac aat acc agt gct ggg ata tgg gaa gga gga ccc agc aag gat<br>Arg Tyr Asn Thr Ser Ala Gly Ile Trp Glu Gly Gly Pro Ser Lys Asp<br>                       405                       410                    415 | 1248 |
| tca ttg tac gtg tcc tct ctc tac ttt acc atg aca agc ctt aca acc<br>Ser Leu Tyr Val Ser Ser Leu Tyr Phe Thr Met Thr Ser Leu Thr Thr<br>                420                       425                    430 | 1296 |
| ata gga ttt gga aac ata gct cct acc aca gat gtg gag aag atg ttt<br>Ile Gly Phe Gly Asn Ile Ala Pro Thr Thr Asp Val Glu Lys Met Phe<br>                435                       440                    445 | 1344 |
| tcg gtg gct atg atg atg gtt ggc tct ctt ctt tat gca act att ttt<br>Ser Val Ala Met Met Met Val Gly Ser Leu Leu Tyr Ala Thr Ile Phe<br>        450                       455                      460 | 1392 |
| gga aat gtt aca aca att ttc cag caa atg tat gcc aac acc aac cga<br>Gly Asn Val Thr Thr Ile Phe Gln Gln Met Tyr Ala Asn Thr Asn Arg<br>465                       470                       475                  480 | 1440 |
| tac cat gag atg ctg aat aat gta cgg gac ttc cta aaa ctc tat cag<br>Tyr His Glu Met Leu Asn Asn Val Arg Asp Phe Leu Lys Leu Tyr Gln<br>                485                       490                    495 | 1488 |
| gtc cca aaa ggc ctt agt gag cga gtc atg gat tat att gtc tca aca<br>Val Pro Lys Gly Leu Ser Glu Arg Val Met Asp Tyr Ile Val Ser Thr<br>        500                       505                      510 | 1536 |
| tgg tcc atg tca aaa ggc att gat aca gaa aag gtc ctc tcc atc tgt<br>Trp Ser Met Ser Lys Gly Ile Asp Thr Glu Lys Val Leu Ser Ile Cys<br>                515                       520                    525 | 1584 |
| ccc aag gac atg aga gct gat atc tgt gtt cat cta aac cgg aag gtt<br>Pro Lys Asp Met Arg Ala Asp Ile Cys Val His Leu Asn Arg Lys Val<br>530                       535                       540 | 1632 |
| ttt aat gaa cat cct gct ttt cga ttg gcc agc gat ggg tgt ctg cgc<br>Phe Asn Glu His Pro Ala Phe Arg Leu Ala Ser Asp Gly Cys Leu Arg<br>545                       550                       555                  560 | 1680 |
| gcc ttg gcg gta gag ttc caa acc att cac tgt gct ccc ggg gac ctc<br>Ala Leu Ala Val Glu Phe Gln Thr Ile His Cys Ala Pro Gly Asp Leu<br>                565                       570                    575 | 1728 |
| att tac cat gct gga gaa agt gtg gat gcc ctc tgc ttt gtg gtg tca<br>Ile Tyr His Ala Gly Glu Ser Val Asp Ala Leu Cys Phe Val Val Ser<br>        580                       585                      590 | 1776 |
| gga tcc ttg gaa gtc atc cag gat gat gag gtg gtg gct att tta ggg<br>Gly Ser Leu Glu Val Ile Gln Asp Asp Glu Val Val Ala Ile Leu Gly<br>                595                       600                    605 | 1824 |
| aag ggt gat gta ttt gga gac atc ttc tgg aag gaa acc acc ctt gcc<br>Lys Gly Asp Val Phe Gly Asp Ile Phe Trp Lys Glu Thr Thr Leu Ala<br>610                       615                       620 | 1872 |
| cat gca tgt gcg aac gtc cgg gca ctg acg tac tgt gac cta cac atc<br>His Ala Cys Ala Asn Val Arg Ala Leu Thr Tyr Cys Asp Leu His Ile | 1920 |

```
                 625                    630                    635                    640
atc aag cgg gaa gcc ttg ctc aaa gtc ctg gac ttt tat aca gct ttt                    1968
Ile Lys Arg Glu Ala Leu Leu Lys Val Leu Asp Phe Tyr Thr Ala Phe
                645                    650                    655 gca aac tcc ttc tca agg aat ctc act ctt act tgc aat ctg agg aaa                    2016
Ala Asn Ser Phe Ser Arg Asn Leu Thr Leu Thr Cys Asn Leu Arg Lys
            660                    665                    670 cgg atc atc ttt cgt aag atc agt gat gtg aag aaa gag gag gag gag                    2064
Arg Ile Ile Phe Arg Lys Ile Ser Asp Val Lys Lys Glu Glu Glu Glu
        675                    680                    685 cgc ctc cgg cag aag aat gag gtg acc ctc agc att ccc gtg gac cac                    2112
Arg Leu Arg Gln Lys Asn Glu Val Thr Leu Ser Ile Pro Val Asp His
    690                    695                    700 cca gtc aga aag ctc ttc cag aag ttc aag cag cag aag gag ctg cgg                    2160
Pro Val Arg Lys Leu Phe Gln Lys Phe Lys Gln Gln Lys Glu Leu Arg
705                    710                    715                    720 aat cag ggc tca aca cag ggt gac cct gag agg aac caa ctc cag gta                    2208
Asn Gln Gly Ser Thr Gln Gly Asp Pro Glu Arg Asn Gln Leu Gln Val
                725                    730                    735 gag agc cgc tcc tta cag aat gga acc tcc atc acc gga acc agc gtg                    2256
Glu Ser Arg Ser Leu Gln Asn Gly Thr Ser Ile Thr Gly Thr Ser Val
            740                    745                    750 gtg act gtg tca cag att act ccc att cag acg tct ctg gcc tat gtg                    2304
Val Thr Val Ser Gln Ile Thr Pro Ile Gln Thr Ser Leu Ala Tyr Val
        755                    760                    765 aaa acc agt gaa tcc ctt aag cag aac aac cgt gat gcc atg gaa ctc                    2352
Lys Thr Ser Glu Ser Leu Lys Gln Asn Asn Arg Asp Ala Met Glu Leu
    770                    775                    780 aag ccc aac ggc ggt gct gac caa aaa tgt ctc aaa gtc aac agc cca                    2400
Lys Pro Asn Gly Gly Ala Asp Gln Lys Cys Leu Lys Val Asn Ser Pro
785                    790                    795                    800 ata aga atg aag aat gga aat gga aaa ggg tgg ctg cga ctc aag aat                    2448
Ile Arg Met Lys Asn Gly Asn Gly Lys Gly Trp Leu Arg Leu Lys Asn
                805                    810                    815 aat atg gga gcc cat gag gag aaa aag gaa gac tgg aat aat gtc act                    2496
Asn Met Gly Ala His Glu Glu Lys Lys Glu Asp Trp Asn Asn Val Thr
            820                    825                    830 aaa gct gag tca atg ggg cta ttg tct gag gac ccc aag agc agt gat                    2544
Lys Ala Glu Ser Met Gly Leu Leu Ser Glu Asp Pro Lys Ser Ser Asp
        835                    840                    845 tca gag aac agt gtg acc aaa aac cca cta agg aaa aca gat tct tgt                    2592
Ser Glu Asn Ser Val Thr Lys Asn Pro Leu Arg Lys Thr Asp Ser Cys
    850                    855                    860 gac agt gga att aca aaa agt gac ctt cgt ttg gat aag gct ggg gag                    2640
Asp Ser Gly Ile Thr Lys Ser Asp Leu Arg Leu Asp Lys Ala Gly Glu
865                    870                    875                    880 gcc cga agt ccg cta gag cac agt ccc atc cag gct gat gcc aag cac                    2688
Ala Arg Ser Pro Leu Glu His Ser Pro Ile Gln Ala Asp Ala Lys His
                885                    890                    895 ccc ttt tat ccc atc ccc gag cag gcc tta cag acc aca ctg cag gaa                    2736
Pro Phe Tyr Pro Ile Pro Glu Gln Ala Leu Gln Thr Thr Leu Gln Glu
            900                    905                    910 gtc aaa cac gaa ctc aaa gag gac atc cag ctg ctc agc tgc aga atg                    2784
Val Lys His Glu Leu Lys Glu Asp Ile Gln Leu Leu Ser Cys Arg Met
        915                    920                    925 act gcc cta gaa aag cag gtg gca gaa att tta aaa ata ctg tcg gaa                    2832
Thr Ala Leu Glu Lys Gln Val Ala Glu Ile Leu Lys Ile Leu Ser Glu
    930                    935                    940 aaa agc gta ccc cag gcc tca tct ccc aaa tcc caa atg cca ctc caa                    2880
```

```
Lys Ser Val Pro Gln Ala Ser Ser Pro Lys Ser Gln Met Pro Leu Gln
945                 950                 955                 960 gta ccc ccc cag ata cca tgt cag gat att ttt agt gtc tca agg cct    2928
Val Pro Pro Gln Ile Pro Cys Gln Asp Ile Phe Ser Val Ser Arg Pro
                965                 970                 975 gaa tca cct gaa tct gac aaa gat gaa atc cac ttt taa                2967
Glu Ser Pro Glu Ser Asp Lys Asp Glu Ile His Phe
            980                 985

<210> SEQ ID NO 2
<211> LENGTH: 988
<212> TYPE: PRT
<213> ORGANISM: Homo sapiens

<400> SEQUENCE: 2

Met Pro Gly Gly Lys Gly Leu Val Ala Pro Gln Asn Thr Phe Leu
 1               5                  10                  15

Glu Asn Ile Val Arg Arg Ser Ser Glu Ser Ser Phe Leu Leu Gly Asn
                20                  25                  30

Ala Gln Ile Val Asp Trp Pro Val Val Tyr Ser Asn Asp Gly Phe Cys
            35                  40                  45

Lys Leu Ser Gly Tyr His Arg Ala Asp Val Met Gln Lys Ser Ser Thr
        50                  55                  60

Cys Ser Phe Met Tyr Gly Glu Leu Thr Asp Lys Lys Thr Ile Glu Lys
 65                 70                  75                  80

Val Arg Gln Thr Phe Asp Asn Tyr Glu Ser Asn Cys Phe Glu Val Leu
                85                  90                  95

Leu Tyr Lys Lys Asn Arg Thr Pro Val Trp Phe Tyr Met Gln Ile Ala
                100                 105                 110

Pro Ile Arg Asn Glu His Glu Lys Val Val Leu Phe Leu Cys Thr Phe
            115                 120                 125

Lys Asp Ile Thr Leu Phe Lys Gln Pro Ile Glu Asp Asp Ser Thr Lys
        130                 135                 140

Gly Trp Thr Lys Phe Ala Arg Leu Thr Arg Ala Leu Thr Asn Ser Arg
145                 150                 155                 160

Ser Val Leu Gln Gln Leu Thr Pro Met Asn Lys Thr Glu Val Val His
                165                 170                 175

Lys His Ser Arg Leu Ala Glu Val Leu Gln Leu Gly Ser Asp Ile Leu
            180                 185                 190

Pro Gln Tyr Lys Gln Glu Ala Pro Lys Thr Pro Pro His Ile Ile Leu
        195                 200                 205

His Tyr Cys Ala Phe Lys Thr Thr Trp Asp Trp Val Ile Leu Ile Leu
210                 215                 220

Thr Phe Tyr Thr Ala Ile Met Val Pro Tyr Asn Val Ser Phe Lys Thr
225                 230                 235                 240

Lys Gln Asn Asn Ile Ala Trp Leu Val Leu Asp Ser Val Val Asp Val
                245                 250                 255

Ile Phe Leu Val Asp Ile Val Leu Asn Phe His Thr Thr Phe Val Gly
            260                 265                 270

Pro Gly Gly Glu Val Ile Ser Asp Pro Lys Leu Ile Arg Met Asn Tyr
        275                 280                 285

Leu Lys Thr Trp Phe Val Ile Asp Leu Leu Ser Cys Leu Pro Tyr Asp
    290                 295                 300

Ile Ile Asn Ala Phe Glu Asn Val Asp Glu Gly Ile Ser Ser Leu Phe
305                 310                 315                 320
```

-continued

```
Ser Ser Leu Lys Val Val Arg Leu Leu Arg Leu Gly Arg Val Ala Arg
            325                 330                 335

Lys Leu Asp His Tyr Leu Glu Tyr Gly Ala Ala Val Leu Val Leu Leu
            340                 345                 350

Val Cys Val Phe Gly Leu Val Ala His Trp Leu Ala Cys Ile Trp Tyr
            355                 360                 365

Ser Ile Gly Asp Tyr Glu Val Ile Asp Glu Val Thr Asn Thr Ile Gln
    370                 375                 380

Ile Asp Ser Trp Leu Tyr Gln Leu Ala Leu Ser Ile Gly Thr Pro Tyr
385                 390                 395                 400

Arg Tyr Asn Thr Ser Ala Gly Ile Trp Glu Gly Pro Ser Lys Asp
            405                 410                 415

Ser Leu Tyr Val Ser Ser Leu Tyr Phe Thr Met Thr Ser Leu Thr Thr
            420                 425                 430

Ile Gly Phe Gly Asn Ile Ala Pro Thr Thr Asp Val Glu Lys Met Phe
            435                 440                 445

Ser Val Ala Met Met Met Val Gly Ser Leu Leu Tyr Ala Thr Ile Phe
    450                 455                 460

Gly Asn Val Thr Thr Ile Phe Gln Gln Met Tyr Ala Asn Thr Asn Arg
465                 470                 475                 480

Tyr His Glu Met Leu Asn Asn Val Arg Asp Phe Leu Lys Leu Tyr Gln
            485                 490                 495

Val Pro Lys Gly Leu Ser Glu Arg Val Met Asp Tyr Ile Val Ser Thr
            500                 505                 510

Trp Ser Met Ser Lys Gly Ile Asp Thr Glu Lys Val Leu Ser Ile Cys
            515                 520                 525

Pro Lys Asp Met Arg Ala Asp Ile Cys Val His Leu Asn Arg Lys Val
            530                 535                 540

Phe Asn Glu His Pro Ala Phe Arg Leu Ala Ser Asp Gly Cys Leu Arg
545                 550                 555                 560

Ala Leu Ala Val Glu Phe Gln Thr Ile His Cys Ala Pro Gly Asp Leu
            565                 570                 575

Ile Tyr His Ala Gly Glu Ser Val Asp Ala Leu Cys Phe Val Val Ser
            580                 585                 590

Gly Ser Leu Glu Val Ile Gln Asp Asp Glu Val Val Ala Ile Leu Gly
            595                 600                 605

Lys Gly Asp Val Phe Gly Asp Ile Phe Trp Lys Glu Thr Thr Leu Ala
            610                 615                 620

His Ala Cys Ala Asn Val Arg Ala Leu Thr Tyr Cys Asp Leu His Ile
625                 630                 635                 640

Ile Lys Arg Glu Ala Leu Leu Lys Val Leu Asp Phe Tyr Thr Ala Phe
            645                 650                 655

Ala Asn Ser Phe Ser Arg Asn Leu Thr Leu Thr Cys Asn Leu Arg Lys
            660                 665                 670

Arg Ile Ile Phe Arg Lys Ile Ser Asp Val Lys Lys Glu Glu Glu
            675                 680                 685

Arg Leu Arg Gln Lys Asn Glu Val Thr Leu Ser Ile Pro Val Asp His
            690                 695                 700

Pro Val Arg Lys Leu Phe Gln Lys Phe Lys Gln Lys Glu Leu Arg
705                 710                 715                 720

Asn Gln Gly Ser Thr Gln Gly Asp Pro Glu Arg Asn Gln Leu Gln Val
            725                 730                 735

Glu Ser Arg Ser Leu Gln Asn Gly Thr Ser Ile Thr Gly Thr Ser Val
```

-continued

```
                        740                 745                 750
Val Thr Val Ser Gln Ile Thr Pro Ile Gln Thr Ser Leu Ala Tyr Val
                755                 760                 765

Lys Thr Ser Glu Ser Leu Lys Gln Asn Asn Arg Asp Ala Met Glu Leu
    770                 775                 780

Lys Pro Asn Gly Gly Ala Asp Gln Lys Cys Leu Lys Val Asn Ser Pro
785                 790                 795                 800

Ile Arg Met Lys Asn Gly Asn Gly Lys Gly Trp Leu Arg Leu Lys Asn
                805                 810                 815

Asn Met Gly Ala His Glu Glu Lys Lys Glu Asp Trp Asn Asn Val Thr
                820                 825                 830

Lys Ala Glu Ser Met Gly Leu Leu Ser Glu Asp Pro Lys Ser Ser Asp
        835                 840                 845

Ser Glu Asn Ser Val Thr Lys Asn Pro Leu Arg Lys Thr Asp Ser Cys
    850                 855                 860

Asp Ser Gly Ile Thr Lys Ser Asp Leu Arg Leu Asp Lys Ala Gly Glu
865                 870                 875                 880

Ala Arg Ser Pro Leu Glu His Ser Pro Ile Gln Ala Asp Ala Lys His
                885                 890                 895

Pro Phe Tyr Pro Ile Pro Glu Gln Ala Leu Gln Thr Thr Leu Gln Glu
            900                 905                 910

Val Lys His Glu Leu Lys Glu Asp Ile Gln Leu Leu Ser Cys Arg Met
        915                 920                 925

Thr Ala Leu Glu Lys Gln Val Ala Glu Ile Leu Lys Ile Leu Ser Glu
    930                 935                 940

Lys Ser Val Pro Gln Ala Ser Pro Lys Ser Gln Met Pro Leu Gln
945                 950                 955                 960

Val Pro Pro Gln Ile Pro Cys Gln Asp Ile Phe Ser Val Ser Arg Pro
                965                 970                 975

Glu Ser Pro Glu Ser Asp Lys Asp Glu Ile His Phe
            980                 985
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:PCR amplification primer

<400> SEQUENCE: 3
atgccggggg gcaagagagg gctg                                          24

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:PCR amplification primer

<400> SEQUENCE: 4
ctgaccctaa gctcataagg atgaac                                        26

<210> SEQ ID NO 5
<211> LENGTH: 26
<212> TYPE: DNA
<213> ORGANISM: Artificial Sequence
<220> FEATURE:

-continued

<223> OTHER INFORMATION: Description of Artificial Sequence:PCR
      amplification primer

<400> SEQUENCE: 5
ccacctcatc atcctggatg acttcc                                          26

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 6
ttaaaagtgg atttcatctt tgtcagattc agg                                  33

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 7
ggggacctca tttaccatgc tggag                                           25

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 8
gattccctca tccacatttt caaaggc                                         27

<210> SEQ ID NO 9
<211> LENGTH: 962
<212> TYPE: PRT
<213> ORGANISM: Homo sapiens
<220> FEATURE:
<223> OTHER INFORMATION: human ether a go-go (Eag) 1 voltage-gated
      potassium channel

<400> SEQUENCE: 9

Met Thr Met Ala Gly Gly Arg Arg Gly Leu Val Ala Pro Gln Asn Thr
  1               5                  10                  15

Phe Leu Glu Asn Ile Val Arg Arg Ser Asn Asp Thr Asn Phe Val Leu
                 20                  25                  30

Gly Asn Ala Gln Ile Val Asp Trp Pro Ile Val Tyr Ser Asn Asp Gly
             35                  40                  45

Phe Cys Lys Leu Ser Gly Tyr His Arg Ala Glu Val Met Gln Lys Ser
     50                  55                  60

Ser Thr Cys Ser Phe Met Tyr Gly Glu Leu Thr Asp Lys Asp Thr Ile
 65                  70                  75                  80

Glu Lys Val Arg Gln Thr Phe Glu Asn Tyr Glu Met Asn Ser Phe Glu
                 85                  90                  95

Ile Leu Met Tyr Lys Lys Asn Arg Thr Pro Val Trp Phe Phe Val Lys
                100                 105                 110

Ile Ala Pro Ile Arg Asn Glu Gln Asp Lys Val Val Leu Phe Leu Cys

```
                115                 120                 125
Thr Phe Ser Asp Ile Thr Ala Phe Lys Gln Pro Ile Glu Asp Asp Ser
    130                 135                 140

Cys Lys Gly Trp Gly Lys Phe Ala Arg Leu Thr Arg Ala Leu Thr Ser
145                 150                 155                 160

Ser Arg Ser Val Leu Gln Gln Leu Ala Pro Ser Val Gln Lys Gly Glu
                165                 170                 175

Asn Val His Lys His Ser Arg Leu Ala Glu Val Leu Gln Leu Gly Ser
            180                 185                 190

Asp Ile Leu Pro Gln Tyr Lys Gln Glu Ala Pro Lys Thr Pro Pro His
        195                 200                 205

Ile Ile Leu His Tyr Cys Val Phe Lys Thr Thr Trp Asp Trp Ile Ile
    210                 215                 220

Leu Ile Leu Thr Phe Tyr Thr Ala Ile Leu Val Pro Tyr Asn Val Ser
225                 230                 235                 240

Phe Lys Thr Arg Gln Asn Asn Val Ala Trp Leu Val Val Asp Ser Ile
                245                 250                 255

Val Asp Val Ile Phe Leu Val Asp Ile Val Leu Asn Phe His Thr Thr
            260                 265                 270

Phe Val Gly Pro Ala Gly Glu Val Ile Ser Asp Pro Lys Leu Ile Arg
        275                 280                 285

Met Asn Tyr Leu Lys Thr Trp Phe Val Ile Asp Leu Leu Ser Cys Leu
    290                 295                 300

Pro Tyr Asp Val Ile Asn Ala Phe Glu Asn Val Asp Glu Gly Ile Ser
305                 310                 315                 320

Ser Leu Phe Ser Ser Leu Lys Val Val Arg Leu Leu Arg Leu Gly Arg
                325                 330                 335

Val Ala Arg Lys Leu Asp His Tyr Ile Glu Tyr Gly Ala Ala Val Leu
            340                 345                 350

Val Leu Leu Val Cys Val Phe Gly Leu Ala Ala His Trp Met Ala Cys
        355                 360                 365

Ile Trp Tyr Ser Ile Gly Asp Tyr Glu Ile Phe Asp Glu Asp Thr Lys
    370                 375                 380

Thr Ile Arg Asn Asn Ser Trp Leu Tyr Gln Leu Ala Met Asp Ile Gly
385                 390                 395                 400

Thr Pro Tyr Gln Phe Asn Gly Ser Gly Ser Gly Lys Trp Glu Gly Gly
                405                 410                 415

Pro Ser Lys Asn Ser Val Tyr Ile Ser Ser Leu Tyr Phe Thr Met Thr
            420                 425                 430

Ser Leu Thr Ser Val Gly Phe Gly Asn Ile Ala Pro Ser Thr Asp Ile
        435                 440                 445

Glu Lys Ile Phe Ala Val Ala Ile Met Met Ile Gly Ser Leu Leu Tyr
    450                 455                 460

Ala Thr Ile Phe Gly Asn Val Thr Thr Ile Phe Gln Gln Met Tyr Ala
465                 470                 475                 480

Asn Thr Asn Arg Tyr His Glu Met Leu Asn Ser Val Arg Asp Phe Leu
                485                 490                 495

Lys Leu Tyr Gln Val Pro Lys Gly Leu Ser Glu Arg Val Met Asp Tyr
            500                 505                 510

Ile Val Ser Thr Trp Ser Met Ser Arg Gly Ile Asp Thr Glu Lys Val
        515                 520                 525

Leu Gln Ile Cys Pro Lys Asp Met Arg Ala Asp Ile Cys Val His Leu
    530                 535                 540
```

-continued

```
Asn Arg Lys Val Phe Lys Glu His Pro Ala Phe Arg Leu Ala Ser Asp
545                 550                 555                 560
Gly Cys Leu Arg Ala Leu Ala Met Glu Phe Gln Thr Val His Cys Ala
            565                 570                 575
Pro Gly Asp Leu Ile Tyr His Ala Gly Glu Ser Val Asp Ser Leu Cys
        580                 585                 590
Phe Val Val Ser Gly Ser Leu Glu Val Ile Gln Asp Asp Glu Val Val
    595                 600                 605
Ala Ile Leu Gly Lys Gly Asp Val Phe Gly Asp Val Phe Trp Lys Glu
610                 615                 620
Ala Thr Leu Ala Gln Ser Cys Ala Asn Val Arg Ala Leu Thr Tyr Cys
625                 630                 635                 640
Asp Leu His Val Ile Lys Arg Asp Ala Leu Gln Lys Val Leu Glu Phe
                645                 650                 655
Tyr Thr Ala Phe Ser His Ser Phe Ser Arg Asn Leu Ile Leu Thr Tyr
            660                 665                 670
Asn Leu Arg Lys Arg Ile Val Phe Arg Lys Ile Ser Asp Val Lys Arg
        675                 680                 685
Glu Glu Glu Glu Arg Met Lys Arg Lys Asn Glu Ala Pro Leu Ile Leu
    690                 695                 700
Pro Pro Asp His Pro Val Arg Arg Leu Phe Gln Arg Phe Arg Gln Gln
705                 710                 715                 720
Lys Glu Ala Arg Leu Ala Ala Glu Arg Gly Gly Arg Asp Leu Asp Asp
                725                 730                 735
Leu Asp Val Glu Lys Gly Asn Val Leu Thr Glu His Ala Ser Ala Asn
            740                 745                 750
His Ser Leu Val Lys Ala Ser Val Val Thr Val Arg Glu Ser Pro Ala
        755                 760                 765
Thr Pro Val Ser Phe Gln Ala Ala Ser Thr Ser Gly Val Pro Asp His
    770                 775                 780
Ala Lys Leu Gln Ala Pro Gly Ser Glu Cys Leu Gly Pro Lys Gly Gly
785                 790                 795                 800
Gly Gly Asp Cys Ala Lys Arg Lys Ser Trp Ala Arg Phe Lys Asp Ala
                805                 810                 815
Cys Gly Lys Ser Glu Asp Trp Asn Lys Val Ser Lys Ala Glu Ser Met
            820                 825                 830
Glu Thr Leu Pro Glu Arg Thr Lys Ala Ser Gly Glu Ala Thr Leu Lys
        835                 840                 845
Lys Thr Asp Ser Cys Asp Ser Gly Ile Thr Lys Ser Asp Leu Arg Leu
    850                 855                 860
Asp Asn Val Gly Glu Ala Arg Ser Pro Gln Asp Arg Ser Pro Ile Leu
865                 870                 875                 880
Ala Glu Val Lys His Ser Phe Tyr Pro Ile Pro Glu Gln Thr Leu Gln
                885                 890                 895
Ala Thr Val Leu Glu Val Arg His Glu Leu Lys Glu Asp Ile Lys Ala
            900                 905                 910
Leu Asn Ala Lys Met Thr Asn Ile Glu Lys Gln Leu Ser Glu Ile Leu
        915                 920                 925
Arg Ile Leu Thr Ser Arg Arg Ser Ser Gln Ser Pro Gln Glu Leu Phe
    930                 935                 940
Glu Ile Ser Arg Pro Gln Ser Pro Glu Ser Glu Arg Asp Ile Phe Gly
945                 950                 955                 960
```

-continued

Ala Ser

HUMAN EAG2

CROSS-REFERENCES TO RELATED APPLICATIONS

This application claims priority to U.S. Ser. No. 60/143,467, filed Jul. 13, 1999, herein incorporated by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The invention provides isolated nucleic acid and amino acid sequences of Eag2, antibodies to Eag2, methods of detecting Eag2, and methods of screening for modulators of Eag2 potassium channels using biologically active Eag2. The invention further provides, in a computer system, a method of screening for mutations of human Eag2 genes as well as a method for identifying a three-dimensional structure of Eag2 polypeptide monomers.

BACKGROUND OF THE INVENTION

Potassium channels are involved in a number of physiological processes, including regulation of heartbeat, dilation of arteries, release of insulin, excitability of nerve cells, and regulation of renal electrolyte transport. Potassium channels are thus found in a wide variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels are made by alpha subunits that fall into 8 families, based on predicted structural and functional similarities (Wei et al., *Neuropharmacology* 35(7):805–829 (1997)). Three of these families (Kv, Eag-related, and KQT) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels, or BK channels have seven transmembrane domains (Meera et al., *Proc. Natl. Acad. Sci. U.S.A.* 94(25):14066–71 (1997)) and are gated by both voltage and calcium or pH (Schreiber et al., *J. Biol. Chem.* 273:3509–16 (1998)). Another family, the inward rectifier potassium channels (Kir), belong to a structural family containing 2 transmembrane domains (see, e.g., Lagrutta et al., *Jpn. Heart. J.* 37:651–660 1996)), and an eighth functionally diverse family (TP, or "two-pore") contains 2 tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels such as those composed of Kv, KQT and Slo or BK alpha subunits have often been found to contain additional, structurally distinct auxiliary, or beta, subunits. These beta subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493:625–633 (1996); Shi et al., *Neuron* 16(4):843–852 (1996)). In another example, the KQT family beta subunit, minK, primarily changes activation kinetics (Sanguinetti et al., *Nature* 384:80–83 (1996)).

The Kv superfamily of voltage-gated potassium channels includes both heteromeric and homomeric channels that are typically composed of four subunits. Voltage-gated potassium channels have been found in a wide variety of tissues and cell types and are involved in processes such as neuronal integration, cardiac pacemaking, muscle contraction, hormone section, cell volume regulation, lymphocyte differentiation, and cell proliferation (see, e.g., Salinas et al., *J. Biol. Chem.* 39:24371–24379 (1997)).

A family of voltage-gated potassium genes, known as the "Eag" or ether à go-go family, was identified on the basis of a Drosophila behavioral mutation with a leg-shaking phenotype (see, e.g., Warmke & Ganetzky, *Proc. Nat'l Acad. Sci. USA* 91:3438–3442 (1994)). Family members from Drosophila and vertebrates have been cloned and fall into three subfamilies. One such subfamily is called the Eag subfamily and is represented, e.g., by Drosophila Eag (Warmke et al., *Science* 252:1560–1562 (1991); Bruggemann et al., *Nature* 365:445–447 (1993)), and rat, mouse, human, and bovine Eags (Ludwig et al., *EMBO J.* 13:4451–4458 (1994); Robertson et al. *Neuropharmacology* 35:841–850 (1996); Occhiodoro et al., *FEBS Letters* 434:177–182 (1998); Shi et al., *J. Physiol.* 115.3:675–682 (1998); Frings et al., *J. Gen Physiol.* 111:583–599 (1998)). A second subfamily, the Erg or "Eag-related gene" family is represented, e.g., by human erg (Shi et al., *J. Neurosci.* 17:9423–9432 (1997)). Finally, a third subfamily, the Elk or "Eag-like K+ gene" is represented, e.g., by Drosophila Elk (Warmke et al., *Proc. Natl. Acad. Sci.* 91:3438–3442 (1994)).

SUMMARY OF THE INVENTION

The present invention thus provides for the first time Eag2, a polypeptide monomer that is an alpha subunit of an voltage-gated potassium channel. Eag2 has not been previously cloned or identified, and the present invention provides the nucleotide and amino acid sequence of human Eag2.

In one aspect, the present invention provides an isolated nucleic acid encoding an alpha subunit of a potassium channel, wherein the subunit: (i) forms, with at least one additional Eag family alpha subunit, a potassium channel having the characteristic of voltage sensitivity; and (ii) comprises an amino acid sequence that has greater than about 70% identity to amino acids 720–988 of a human Eag2 amino acid sequence or comprises an amino acid sequence that has greater than about 85% identity to the amino acid sequence of SEQ ID NO:2.

In another aspect, the present invention provides an isolated nucleic acid that selectively hybridizes under moderately stringent hybridization conditions to a nucleotide sequence of SEQ ID NO:1.

In another aspect, the present invention provides an isolated nucleic acid that selectively hybridizes under stringent conditions to a nucleotide sequence of SEQ ID NO:1 or to a nucleotide sequence encoding an amino acid sequence of SEQ ID NO:2.

In another aspect, the present invention provides a method of detecting a nucleic acid, by contacting the nucleic acid with a nucleic acid of the invention.

In another aspect, the present invention provides an isolated alpha subunit of a potassium channel, wherein the subunit: (i) forms, with at least one additional Eag family alpha subunit, a potassium channel having the characteristic of voltage sensitivity; (ii) comprises an amino acid sequence that has greater than about 70% identity to amino acids 720–988 of a human Eag2 amino acid sequence or comprises an amino acid sequence that has greater than about 85% identity to the amino acid sequence of SEQ ID NO:2.

In one embodiment, the polypeptide specifically binds to polyclonal antibodies generated against SEQ ID NO:2.

In one embodiment, the nucleic acid encodes human Eag2. In another embodiment, the nucleic acid encodes SEQ ID NO:2. In another embodiment, the nucleic acid has the nucleotide sequence of SEQ ID NO:1. In another embodiment, the nucleic acid is amplified by primers that selectively hybridize under stringent hybridization conditions to the same sequence as primers selected from the group consisting of:

ATGCCGGGGGGCAAGAGAGGGCTG (SEQ ID NO:3);

CTGACCCTAAGCTCATAAGGATGAAC (SEQ ID NO:4);

CCACCTCATCATCCTGGATGACTTCC (SEQ ID NO:5),

TTAAAAGTGGATTTCATCTTTGTCAGATTCAGG (SEQ ID NO:6);

GGGGACCTCATTTACCATGCTGGAG (SEQ ID NO:7); and

GATTCCCTCATCCACATTTTCAAAGGC (SEQ ID NO:8).

In another embodiment, the polypeptide monomer has a molecular weight of between about 109 kD and about 119 kD. In another embodiment, the polypeptide monomer has the sequence of SEQ ID NO:2.

In another embodiment, the polypeptide monomer comprises an alpha subunit of a heteromeric or homomeric potassium channel.

In another aspect, the present invention provides an expression vector comprising the isolated nucleic acid and a host cell transfected with such an expression vector.

In another aspect, the present invention provides an antibody that selectively binds to the isolated polypeptide monomer.

In another aspect, the present invention provides a method for identifying a compound that increases or decreases ion flux through a potassium channel, the method comprising the steps of: (i) contacting the compound with an alpha subunit of a potassium channel, wherein the subunit: (a) forms, with at least one additional Eag family alpha subunit, a potassium channel having a characteristic of voltage sensitivity; and (b) comprises an amino acid sequence that has greater than about 70% to amino acids 720–988 of a human Eag2 amino acid sequence or comprises an amino acid sequence that has greater than about 85% identity to the amino acid sequence of SEQ ID NO:2; and (ii) determining the functional effect of the compound upon the potassium channel.

In one embodiment, the functional effect is determined by measuring changes in ion flux, current, voltage, or ion concentration. In another embodiment, the polypeptide monomer is recombinant.

In one embodiment, the functional effect is a physical effect. In another embodiment, the functional effect is a chemical effect. In another embodiment, the functional effect is determined by measuring ligand binding to the channel.

In one embodiment, the polypeptide is expressed in a cell or cell membrane, e.g., a eukaryotic cell or a human cell. In another embodiment, the polypeptide is attached to a solid support.

In another aspect, the present invention provides a method of detecting the presence of human Eag2 in a biological sample, the method comprising the steps of: (i) isolating a biological sample; (ii) contacting the biological sample with a human Eag2-specific reagent that selectively associates with human Eag2; and, (iii) detecting the level of human Eag2-specific reagent that selectively associates with the sample.

In one embodiment, the human Eag 2-specific reagent is selected from the group consisting of: Eag 2-specific antibodies, Eag 2-specific oligonucleotide primers, and Eag 2-specific nucleic acid probes.

In another aspect, the present invention provides, in a computer system, a method of screening for mutations of a human Eag2 gene, the method comprising the steps of: (i) entering into the system at least about 50 nucleotides of a first nucleic acid sequence encoding a human Eag2 gene having a nucleotide sequence of SEQ ID NO:1, and conservatively modified variants thereof; (ii) comparing the first nucleic acid sequence with a second nucleic acid sequence having substantial identity to the first nucleic acid sequence; and (iii) identifying nucleotide differences between the first and second nucleic acid sequences.

In one embodiment, the second nucleic acid sequence is associated with a disease state. In another embodiment, the step of entering comprises entering into the system a nucleotide sequence corresponding to amino acids 720–988 of a human Eag2 gene encoding polypeptide having an amino acid sequence of SEQ ID NO:2.

In another aspect, the present invention provides a method for identifying a compound that increases or decreases ion flux through a potassium channel comprising an Eag2 polypeptide, the method comprising the steps of: (i) entering into a computer system an amino acid sequence of at least 50 amino acids of an Eag2 polypeptide or at least 150 nucleotides of a nucleic acid encoding the Eag2 polypeptide, the Eag2 polypeptide comprising a subsequence having at least 70% amino acid sequence to amino acids 720 to 988 of SEQ ID NO:2 or comprises an amino acid sequence that has greater than about 85% identity to the amino acid sequence of SEQ ID NO:2; (ii) generating a three-dimensional structure of the polypeptide encoded by the amino acid sequence; (iii) generating a three-dimensional structure of the potassium channel comprising the Eag2 polypeptide; (iv) generating a three-dimensional structure of the compound; and (v) comparing the three-dimensional structures of the polypeptide and the compound to determine whether or not the compound binds to the polypeptide.

In another aspect, the present invention provides a method of modulating ion flux through an Eag potassium channel to treat disease in a subject, the method comprising the step of administering to the subject a therapeutically effective amount of a compound identified using the methods of the invention.

BRIEF DESCRIPTION OF THE DRAWINGS

FIG. 1: Amino acid alignment of human Eag2 and human Eag1. Identical amino acids are shaded. Amino acid positions are given at the left margin. The region of highest homology extends from the amino terminus through amino acid 720 of the Eag2 sequence. This region includes the "core" of the channel, six transmembrane domains and a P-region that contributes to the channel pore, and a putative cyclic-nucleotide binding domain in the C-terminal cytoplasmic region. Within this region, Eag2 and Eag1 share 85% amino acid identity. The homology drops off significantly from this region to the C-terminus (amino acids 720–998 of Eag2).

FIG. 2: Functional expression of Eag2 in *Xenopus oocytes*. A.) Families of outward currents recorded from an oocyte injected with Eag2 cRNA. Voltage steps ranged from −80 mV to +40 mV in 10 mV increments; the holding potential was −90 mV and tail currents were elicited at −60 mV. B.) A normalized conductance vs. voltage curve for the Eag2 current shown in A. The line shows a bolztmann fit to the data, and gives a half-activation voltage ($V_{50}$) of −28.5 mV. Note the low slope of the curve and very hyperpolarized activation of the current. C.) Sensitivity of the activation rate of Eag2 to holding potential. Eag2 currents were activated by a step to 0 mV from holding potentials that varied from −120 mV to −40 mV in 20 mV increments. Activation had both fast and slow components, with the slow component dominating at hyperpolarized holding potentials and the fast component dominating at holding potentials near typical cellular resting potentials.

DETAILED DESCRIPTION OF THE INVENTION

I. Introduction

Figure 3:
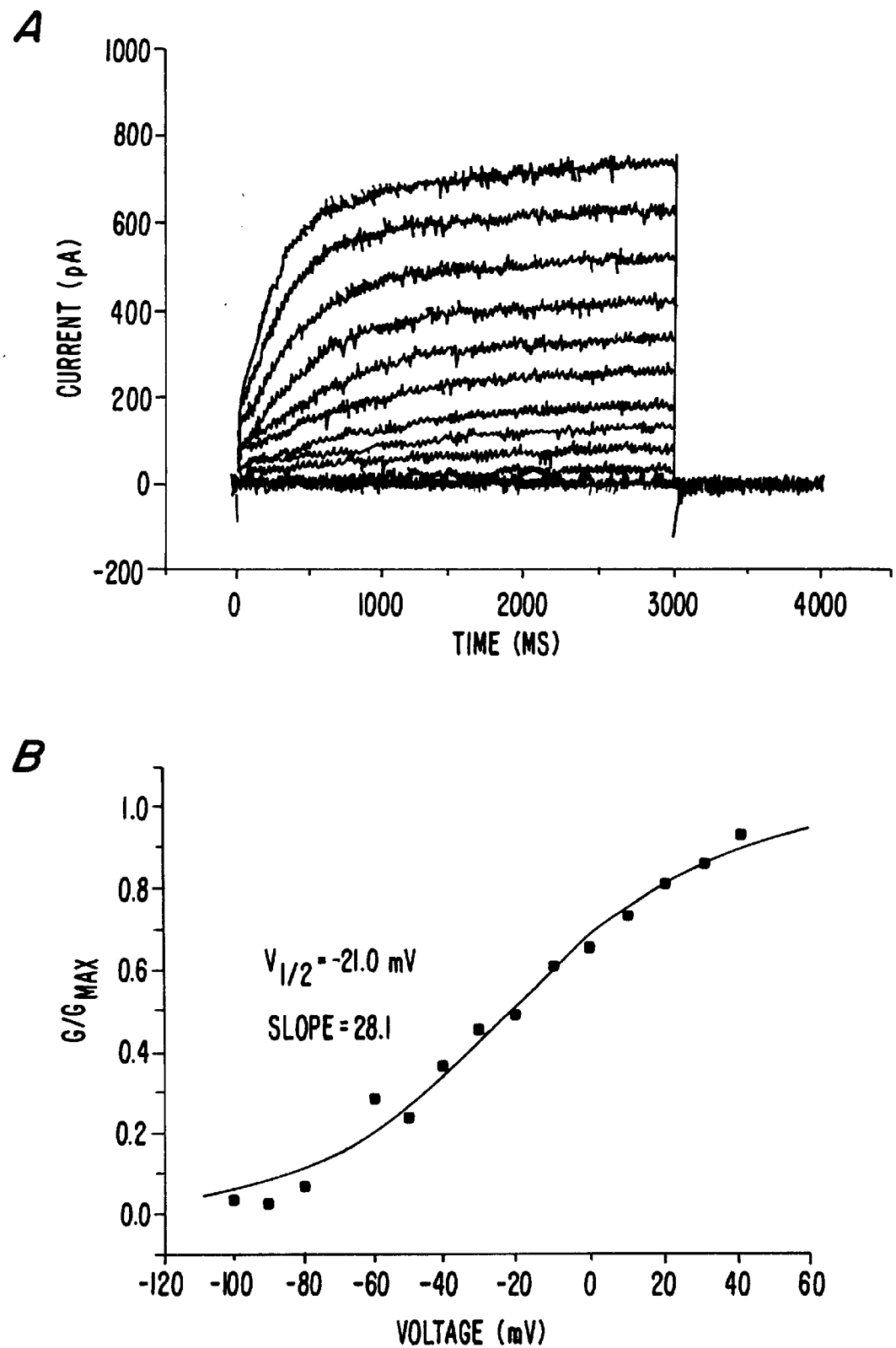
FIG. 3: Transient expression of Eag2 in Chinese hamster ovary cells. A.) Families of outward currents recorded by whole patch clamp from a CHO cell transfected with Eag2. The holding potential was −90 mV and voltage steps ranged from −100 mV to +40 mV in 10 mV increments. Tail currents were measured at −120 mV. B.) A normalized conductance vs. voltage curve for the currents shown in A. The line shows a boltzmann fit of the data, and gives a $V_{50}$ of −21 mV. The $V_{50}$ and slope are similar to that found for Eag2 expression in *Xenopus oocytes*.

The present invention provides for the first time a nucleic acid encoding Eag2, identified and cloned from human tissue. This polypeptide monomer is a member of the "Kv" superfamily of potassium channel monomers and the "Eag" (ether à go-go) family and subfamily of potassium channel monomers. Members of this family are polypeptide monomers that are subunits of voltage-gated potassium channels having six transmembrane regions (K=potassium, v=voltage-gated). Voltage-gated potassium channels have significant roles in maintaining the resting potential and in controlling excitability of a cell.

The invention also provides methods of screening for activators and inhibitors of voltage-gated potassium channels that contain an Eag2 subunit. Such modulators of voltage-gated channel activity are useful for treating disorders involving abnormal ion flux, e.g., CNS disorders such as migraines, hearing and vision problems, Alzheimer's disease, learning and memory disorders, seizures, psychotic disorders, and as neuroprotective agents (e.g., to prevent stroke).

Furthermore, the invention provides assays for Eag2 activity where Eag2 acts as a direct or indirect reporter molecule. Such uses of Eag2 as a reporter molecule in assay and detection systems have broad applications, e.g., Eag2 can be used as a reporter molecule to measure changes in potassium concentration, membrane potential, current flow, ion flux, transcription, signal transduction, receptor-ligand interactions, second messenger concentrations, in vitro, in vivo, and ex vivo. In one embodiment, Eag2 can be used as an indicator of current flow in a particular direction (e.g., outward or inward potassium flow), and in another embodiment, Eag2 can be used as an indirect reporter via attachment to a second reporter molecule such as green fluorescent protein.

The invention also provides for methods of detecting Eag2 nucleic acid and protein expression, allowing investigation of the channel diversity provided by hEag2, as well as diagnosis of disease caused by abnormal ion flux, e.g., CNS disorders such as migraines, hearing and vision problems, seizures, and psychotic disorders.

Finally, the invention provides for a method of screening for mutations of Eag2 genes or proteins. The invention includes, but is not limited to, methods of screening for mutations in Eag2 with the use of a computer. Similarly, the invention provides for methods of identifying the three-dimensional structure of Eag2, as well as the resulting computer readable images or data that comprise the three dimensional structure of Eag2. Other methods for screening for mutations of Eag2 genes or proteins include high density oligonucleotide arrays, PCR, immunoassays and the like.

Functionally, Eag2 is an alpha subunit of an voltage-gated potassium channel. Typically, such voltage-gated channels are heteromeric or homomeric and contain four alpha subunits or monomers each with six transmembrane domains. Heteromeric Eag channels can comprise one or more Eag2 alpha subunits along with one or more additional alpha subunits from the Eag family, preferably from the Eag subfamily, such as Eag1. Eag2 channels may also be homomeric. In addition, such channels may comprise one or more auxiliary beta subunits. The presence of Eag2 in an voltage-gated potassium channel may also modulate the activity of the heteromeric channel and thus enhance channel diversity. Channel diversity is also enhanced with alternatively spliced forms of Eag2.

Structurally, the nucleotide sequence of human Eag2 (SEQ ID NO:1) encodes a polypeptide monomer of approximately 988 amino acids with a predicted molecular weight of approximately 114 kDa (SEQ ID NO:2) and a predicted range of 109–119 kDa. In particular, the amino acid sequence of hEag2 has an "C-terminal" region (approximately amino acids 720 to the end of the amino acid sequence, see, e.g., amino acids 720–988 of SEQ ID NO:2, hEag2) that distinguishes Eag2 from other Eag family members. Related Eag2 genes from other species share at least about 70%, preferably 75, 80, 85, 90, or 95% amino acid identity in this region. Furthermore, related Eag2 genes from other species share about 85% identity to the amino acid sequence of SED ID NO:2.

The present invention also provide polymorphic variants of the hEag2 depicted in SEQ ID NO:2: variant #1, in which an isoleucine residue is substituted for the valine residue at amino acid position 973; variant #2, in which a lysine residue is substituted for the arginine residue at amino acid position 927; variant #3, in which an alanine residue is substituted for the threonine residue at amino acid position 905, and variant #4, in which an isoleucine residue is substituted for the valine residue at amino acid position 40.

Specific regions of the hEag2 nucleotide and amino acid sequence may be used to identify polymorphic variants, interspecies homologs, and alleles of hEag2. This identification can be made in vitro, e.g., under stringent hybridization conditions and sequencing, or by using the sequence information in a computer system for comparison with other nucleotide sequences, or by using antibodies raised against hEag2. Typically, identification of polymorphic variants and alleles of hEag2 is made by comparing the amino acid sequence (or the nucleic acid sequence encoding the nucleic acid sequence) of the "C-terminal region" (approximately amino acids 720–988 of hEag2, see SEQ ID NO:2 for example). Amino acid identity of approximately at least 70% or above, preferably 75%, 80%, or 85%, most preferably 90–95% or above in the C-terminal region typically demonstrates that a protein is a polymorphic variant, interspecies homolog, or allele of hEag2. Alternatively, amino acid sequence identity of at least 85% or above to the amino acid sequence of SEQ ID NO:2 typically demonstrates that a protein is a polymorphic variant, interspecies homolog, or allele of hEag2. Sequence comparison can be performed using any of the sequence comparison algorithms discussed below. Antibodies that bind specifically to the subunit association region of hEag2 can also be used to identify alleles, interspecies homologs, and polymorphic variants.

Polymorphic variants, interspecies homologs, and alleles of hEag2 can be confirmed by expressing or co-expressing the putative Eag2 polypeptide monomer and examining whether it forms a potassium channel with Eag2/Eag functional characteristics, such as voltage-gating. This assay is used to demonstrate that a protein having about 70% or greater, preferably 75%, 80%, 85%, 90%, or 95% or greater amino acid identity to the "C-terminal" region of hEag2 shares the same functional characteristics as hEag2 and is therefore a species of hEag2. This assay is also used to demonstrate that a protein having about 85% or greater, preferably 90%, or 95% or greater amino acid identity to the amino acid sequence of SEQ ID NO:2 shares the same functional characteristics as hEag2 and is therefore a species of hEag2. Typically, hEag2 having the amino acid sequence of SEQ ID NO:2 is used as a positive control in comparison to the putative Eag2 protein to demonstrate the identification of a polymorphic variant, interspecies homolog, or allele of hEag2.

Eag2 nucleotide and amino acid sequence information may also be used to construct models of voltage-gated potassium channels in a computer system. These models are subsequently used to identify compounds that can activate or inhibit voltage-gated potassium channels comprising Eag2. Such compounds that modulate the activity of channels comprising Eag2 can be used to investigate the role of Eag2 in modulation of channel activity and in channel diversity.

The isolation of biologically active Eag2 for the first time provides a means for assaying for inhibitors and activators of voltage-gated potassium channels that comprise Eag2 subunits. Biologically active Eag2 is useful for testing inhibitors and activators of voltage-gated potassium channels comprising subunits of Eag2 and other Eag family members using in vivo and in vitro expression that measure, e.g., changes in ion flux, ion concentration, voltage, current, or ligand binding. Such activators and inhibitors identified using an voltage-gated potassium channel comprising at least one Eag2 subunit, preferably four Eag2 subunits, can be used to further study voltage gating, channel kinetics and conductance properties of potassium channels. Such activators and inhibitors are useful as pharmaceutical agents for treating diseases involving abnormal ion flux, e.g., CNS disorders, as described above. Methods of detecting Eag2 and expression of channels comprising Eag2 are also useful for diagnostic applications for diseases involving abnormal ion flux, e.g., CNS disorders and other disorders. For example, chromosome localization of the gene encoding human Eag2 can be used to identify diseases caused by and associated with hEag2. Methods of detecting Eag2 are also useful for examining the role of Eag2 in channel diversity and modulation of channel activity.

II. Definitions

As used herein, the following terms have the meanings ascribed to them unless specified otherwise.

The phrase "voltage-gated" activity or "voltage-gating" refers to a characteristic of a potassium channel composed of individual polypeptide monomers or subunits. Generally, the probability of a voltage-gated potassium channel opening increases as a cell is depolarized. Voltage-gated potassium channels primarily allow efflux of potassium because they have greater probabilities of being open at membrane potentials more positive than the membrane potential for potassium ($E_K$) in typical cells. $E_K$, or the membrane potential for potassium, depends on the relative concentrations of potassium found inside and outside the cell membrane, and is typically between −60 and −100 mV for mammalian cells. $E_K$ is the membrane potential at which there is no net flow of potassium ion because the electrical potential (i.e., voltage potential) driving potassium influx is balanced by the concentration gradient ( the [$K^+$] potential) directing potassium efflux. This value is also known as the "reversal potential" or the "Nernst" potential for potassium. Some voltage-gated potassium channels undergo inactivation, which can reduce potassium efflux at higher membrane potentials. Potassium channels can also allow potassium influx in certain instances when they remain open at membrane potentials negative to $E_K$ (see, e.g., Adams & Nonner, in *Potassium Channels*, pp. 40–60 (Cook, ed., 1990)). The characteristic of voltage gating can be measured by a variety of techniques for measuring changes in current flow and ion flux through a channel, e.g., by changing the [$K^+$] of the external solution and measuring the activation potential of the channel current (see, e.g., U.S. Pat. No. 5,670,335), by measuring current with patch clamp techniques or voltage clamp under different conditions, and by measuring ion flux with radiolabeled tracers or voltage-sensitive dyes under different conditions.

"Homomeric channel" refers to an Eag2 channel composed of identical alpha subunits, whereas "heteromeric channel" refers to an Eag channel composed of at least one Eag2 alpha subunit plus at least one other different type of alpha subunit from a related gene family such as the Eag family, preferably from the Eag subfamily, e.g., Eag1. Both homomeric and heteromeric channels can include auxiliary beta subunits. Typically, the channel is composed of four alpha subunits and the channel can be heteromeric or homomeric.

A "beta subunit" is a polypeptide monomer that is an auxiliary subunit of a potassium channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits comprising the pore region. They can also contribute to the external mouth of the pore region.

The phrase "C-terminal region" refers to the region of Eag2 that structurally identifies this particular protein (approximately amino acids 720–988 of hEag2, see SEQ ID NO:2). This region can be used to identify Eag2 polymorphic variants and Eag2 alleles of hEag2, through amino acid sequence identity comparison using a sequence comparison algorithm such as BLASTP.

"Eag2" refers to a polypeptide that is a subunit or monomer of an voltage-gated potassium channel, a member of the Eag family and subfamily, and a member of the Kv superfamily of potassium channel monomers. When Eag2 is part of a potassium channel, either a homomeric or heteromeric potassium channel, the channel has voltage-gated activity. The term Eag2 therefore refers to polymorphic variants, alleles, mutants, and interspecies homologs that: (1) have a C-terminal region that has greater than about 70% amino acid sequence identity, preferably about 75, 80, 85, 90, or 95% amino acid sequence identity, to a hEag2 C-terminal region or comprises an amino acid sequence that has greater than about 85% identity to the amino acid sequence of SEQ ID NO:2; (2) bind to antibodies raised against an immunogen comprising an amino acid sequence selected from the group consisting of SEQ ID NO:2, amino acids 720–988 of SEQ ID NO:2, and conservatively modified variants thereof; (3) specifically hybridize under stringent hybridization conditions to a sequence selected from the group consisting of SEQ ID NO:1, the nucleotide sequence encoding amino acids 720–988 of SEQ ID NO:2, and conservatively modified variants thereof; or (4) are amplified by primers that specifically hybridize under stringent hybridization conditions to the same sequence as a primer set consisting of SEQ ID NO:3, SEQ ID NO:4, SEQ ID NO:5, SEQ ID NO:6, SEQ ID NO:7, and SEQ ID NO:8.

The phrase "functional effects" in the context of assays for testing compounds affecting a channel comprising Eag2 includes the determination of any parameter that is indirectly or directly under the influence of the channel. It includes changes in ion flux and membrane potential, changes in ligand binding, and also includes other physiologic effects such as increases or decreases of transcription or hormone release.

"Determining the functional effect" refers to examining the effect of a compound that increases or decreases ion flux on a cell or cell membrane in terms of cell and cell membrane function. The ion flux can be any ion that passes through a channel and analogues thereof, e.g., potassium, rubidium, sodium. Preferably, the term refers to the functional effect of the compound on the channels comprising hEag2, e.g., changes in ion flux including radioisotopes, current amplitude, ligand binding, membrane potential, current flow, transcription, protein binding, phosphorylation, dephosphorylation, second messenger concentrations (cAMP, cGMP, $Ca^{2+}$, $IP_3$) and other physiological effects such as hormone and neurotransmitter release, as well as changes in voltage and current. Such functional effects can be measured by any means known to those skilled in the art, e.g., patch clamping, voltage-sensitive dyes, whole cell currents, radioisotope efflux, inducible markers, and the like.

"Inhibitors," "activators" or "modulators" of voltage-gated potassium channels comprising hEag2 refer to inhibitory or activating molecules identified using in vitro and in vivo assays for hbEag2 channel function. Inhibitors are compounds that decrease, block, prevent, delay activation, inactivate, desensitize, or down regulate the channel. Activators are compounds that increase, open, activate, facilitate, enhance activation, sensitize or up regulate channel activity. Such assays for inhibitors and activators include e.g., expressing hEag2 in cells or cell membranes and then measuring flux of ions through the channel and determining changes in polarization (i.e., electrical potential). Alternatively, cells expressing endogenous hEag2 channels can be used in such assays. To examine the extent of inhibition, samples or assays comprising an hEag2 channel are treated with a potential activator or inhibitor and are compared to control samples without the inhibitor. Control samples (untreated with inhibitors) are assigned a relative hEag2 activity value of 100%. Inhibition of channels comprising hEag2 is achieved when the hEag2 activity value relative to the control is about 90%, preferably 50%, more preferably 25–0%. Activation of channels comprising hEag2 is achieved when the hEag2 activity value relative to the control is 110%, more preferably 150%, most preferably at least 200–500% higher or 1000% or higher.

"Biologically active" hEag2 refers to hEag2 that has the ability to form a potassium channel having the characteristic of voltage-gating tested as described above.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated hEag2 nucleic acid is separated from open reading frames that flank the hEag2 gene and encode proteins other than hEag2. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by readthrough transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095–35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The subunits and potassium channels of the invention comprise domain such as a "pore" domain. These domains can be structurally identified using methods known to those of skill in the art, such as sequence analysis programs that identify hydrophobic and hydrophilic domains (see, e.g., Kyte & Doolittle, *J. Mol. Biol.* 157:105–132 (1982)). Such domains are useful for making chimeric proteins and for in vitro assays of the invention.

A "label" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radiolabel into the peptide, and used to detect antibodies specifically reactive with the peptide).

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, preferably 75%, 80%, 85%, 90%, or 95% identity over a specified region such as the hEag2 C-terminal region or 85% identity or more to the amino acid sequence of SEQ ID NO:2), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 50 amino acids or nucleotides in length, or more preferably over a region that is 75–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to Eag2 nucleic acids and proteins, e.g., hEag2, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff& Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cased, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552–554 (1990)).

For preparation of monoclonal or polyclonal antibodies, any technique known in the art can be used (see, e.g., Kohler & Milstein, Nature 256:495–497 (1975); Kozbor et al., Immunology Today 4: 72 (1983); Cole et al., pp. 77–96 in Monoclonal Antibodies and Cancer Therapy, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348:552–554 (1990); Marks et al., Biotechnology 10:779–783 (1992)).

An "anti- hEag2" antibody is an antibody or antibody fragment that specifically binds a polypeptide encoded by the hEag2 gene, cDNA, or a subsequence thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to hEag2, encoded in SEQ ID NO:2, splice variants, or portions thereof, can be selected to obtain only those polyclonal antibodies that are specifically immunoreactive with hEag2 and not with other proteins, except for polymorphic variants and alleles of hEag2. This selection may be achieved by subtracting out antibodies that cross-react with molecules such as rat Eag1, Drosophila Eag, mouse Eag1, and human Eag1. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as E. coli, or eukaryotic cells such as yeast, insect, amphibian, or mammalian cells such as CHO, HeLa and the like, e.g., cultured cells, explants, and cells in vivo.

"Biological sample" as used herein is a sample of biological tissue or fluid that contains hEag2 or nucleic acid encoding hEag2 protein. Such samples include, but are not limited to, tissue isolated from humans. Biological samples may also include sections of tissues such as frozen sections taken for histologic purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

III. Isolating the Gene Encoding EAG2

A. General Recombinant DNA Methods

This invention relies on routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859–1862 (1981), using an automated synthesizer, as described in Van Devanter et. al., Nucleic Acids Res. 12:6159–6168 (1984). Purification of oligonueleotides is by either native acrylamide gel electrophoresis or by anion-exchange HPLC as described in Pearson & Reanier, J. Chrom. 255:137–149 (1983).

The sequence of the cloned genes and synthetic oligonucleotides can be verified after cloning using, e.g., the chain termination method for sequencing double-stranded templates of Wallace et al., Gene 16:21–26 (1981).

B. Cloning Methods for the Isolation of Nucleotide Sequences Encoding hEag2

In general, the nucleic acid sequences encoding Eag2 and related nucleic acid sequence homologs are cloned from cDNA and genomic DNA libraries or isolated using amplification techniques with oligonucleotide primers. For example, hEag2 sequences are typically isolated from human nucleic acid (genomic or cDNA) libraries by hybridizing with a nucleic acid probe or polynucleotide, the sequence of which can be derived from SEQ ID NO:1, optionally from the region encoding the C-terminal region. A suitable tissue from which Eag2 RNA and cDNA can be isolated is brain tissue, e.g., whole brain or hippocampus.

Amplification techniques using primers can also be used to amplify and isolate Eag2 from DNA or RNA. The following primers can also be used to amplify a sequence of hEag2: ATGCCGGGGGGCAAGAGAGGGCTG (SEQ ID NO:3), CTGACCCTAAGCTCATAAGGATGAAC (SEQ ID NO:4) CCACCTCATCATCCTGGATGACTTCC (SEQ ID NO:5), TTAAAAGTGGATTTCATCTTTGTCAGATTCAGG (SEQ ID NO:6) GGGGACCTCATTTACCATGCTGGAG (SEQ ID NO:7) and GATTCCCTCATCCACATTTTCAAAGGC (SEQ ID NO:8). These primers can be used, e.g., to amplify either the full length sequence or a probe of one to several hundred nucleotides, which is then used to screen a human library for full-length hEag2.

Nucleic acids encoding Eag2 can also be isolated from expression libraries using antibodies as probes. Such polyclonal or monoclonal antibodies can be raised using the sequence of SEQ ID NO:2.

Human Eag2 polymorphic variants and alleles that are substantially identical to the C-terminal region of hEag2 can be isolated using hEag2 nucleic acid probes and oligonucleotides under stringent hybridization conditions, by screening libraries. Alternatively, expression libraries can be used to clone Eag2 and Eag2 polymorphic variants and alleles by detecting expressed homologs immunologically with antisera or purified antibodies made against hEag2 or portions thereof (e.g., the C-terminal region of hEag2), which also recognize and selectively bind to the Eag2 homolog.

To make a cDNA library, one should choose a source that is rich in Eag2 mRNA, e.g., tissue such as brain, e.g., whole brain or hippocampus. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating Eag2 nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of Eag2 directly from mRNA, from cDNA, from genomic libraries or cDNA libraries. Degenerate oligonucleotides can be designed to amplify hEag2 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of Eag2 encoding mRNA in physiological samples, for nucleic acid sequencing, or for other purposes. Genes amplified by the PCR reaction can be purified from agarose gels and cloned into an appropriate vector.

Gene expression of Eag2 can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology and the like.

Synthetic oligonucleotides can be used to construct recombinant Eag2 genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the Eag2 gene. The specific subsequence is then ligated into an expression vector.

The gene for Eag2 is typically cloned into intermediate vectors before transformation into prokaryotic or eukaryotic cells for replication and/or expression. These intermediate vectors are typically prokaryote vectors, e.g., plasmids, or shuttle vectors.

C. Expression in Prokaryotes and Eukaryotes

To obtain high level expression of a cloned gene, such as those cDNAs encoding Eag2, one typically subclones Eag2 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al., supra. Bacterial expression systems for expressing the Eag2 protein are available in, e.g., *E. coli*, Bacillus sp., and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the Eag2 encoding nucleic acid in host cells. A typical expression cassette thus contains a promoter operably linked to the nucleic acid sequence encoding Eag2 and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a Eag2 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of Eag2 protein, which are then purified using standard techniques (see, e.g., Colley et al., *J. Biol. Chem.* 264:17619–17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing Eag2.

After the expression vector is introduced into the cells, the transfected cells are cultured under conditions favoring expression of Eag2, which is recovered from the culture using standard techniques identified below.

IV. Purification of Eag2 Polypeptides

Either naturally occurring or recombinant Eag2 can be purified for use in functional assays. Naturally occurring Eag2 monomers can be purified, e.g., from human tissue such as whole brain or hippocampus, and any other source of a Eag2 homolog. Recombinant Eag2 monomers can be purified from any suitable expression system.

The Eag2 monomers may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant Eag2 monomers are being purified. For example, proteins having established molecular adhesion properties can be reversible fused to the Eag2 monomers. With the appropriate ligand, the Eag2 monomers can be selectively adsorbed to a purification column and then freed from the column in a relatively pure form. The fused protein is then removed by enzymatic activity. Finally the Eag2 monomers could be purified using immunoaffinity columns.

A. Purification of Eag2 Monomers from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of the Eag2 monomers inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM MgCl$_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human Eag2 monomers are separated from other bacterial proteins by standard separation techniques, e.g., with Ni-NTA agarose resin.

Alternatively, it is possible to purify the Eag2 monomers from bacteria periplasm. After lysis of the bacteria, when the Eag2 monomers are exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying the Eag2 Monomers

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the Eag2 monomers can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The Eag2 monomers can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of Eag2

In addition to the detection of Eag2 genes and gene expression using nucleic acid hybridization technology, one can also use immunoassays to detect the Eag2 monomers. Immunoassays can be used to qualitatively or quantitatively analyze the Eag2 monomers. A general overview of the applicable technology can be found in Harlow & Lane, *Antibodies: A Laboratory Manual* (1988).

A. Antibodies to Eag2 Monomers

Methods of producing polyclonal and monoclonal antibodies that react specifically with the Eag2 monomers are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of immunogens comprising portions of Eag2 monomers may be used to produce antibodies specifically reactive with Eag2 monomers. For example, recombinant Eag2 monomers or an antigenic fragment thereof, such as the C-terminal region, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-Eag2 proteins, other Eag1 orthologs such as human Eag1 or related subfamily members such as rat Eag2), using a competitive binding immunoassay. Specific polyclonal antisera and monoclonal antibodies will usually bind with a $K_d$ of at least about 0.1 mM, more usually at least about 1 $\mu$M, preferably at least about 0.1 $\mu$M or better, and most preferably, 0.01 $\mu$M or better.

Once the specific antibodies against a Eag2 are available, the Eag2 can be detected by a variety of immunoassay methods. For a review of immunological and immunoassay procedures, see *Basic and Clinical Immunology* (Stites & Terr eds., $7^{th}$ ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

The Eag2 can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., $7^{th}$ ed. 1991). Immunological binding assays (or immunoassays) typically use an antibody that specifically binds to a protein or antigen of choice (in this case the Eag2 or an antigenic subsequence thereof). The antibody (e.g., anti-Eag2) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled Eag2 polypeptide or a labeled anti-Eag2 antibody. Alternatively, the labeling agent may be a third moiety, such a secondary antibody, which specifically binds to the antibody/Eag2 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting the Eag2 in samples may be either competitive or noncompetitive. Noncompetitive immunoassays are assays in which the amount of antigen is directly measured. In one preferred "sandwich" assay, for example, the anti-Eag2 subunit antibodies can be bound directly to a solid substrate on which they are immobilized. These immobilized antibodies then capture Eag2 present in the test sample. The Eag2 monomers are thus immobilized and then bound by a labeling agent, such as a second Eag2 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of the Eag2 present in the sample is measured indirectly by measuring the amount of known, added (exogenous) Eag2 displaced (competed away) from an anti- Eag2 antibody by the unknown Eag2 present in a sample. In one competitive assay, a known amount of the Eag2 is added to a sample and the sample is then contacted with an antibody that specifically binds to the Eag2. The amount of exogenous Eag2 bound to the antibody is inversely proportional to the concentration of the Eag2 present in the sample. In a particularly preferred embodiment, the antibody is immobilized on a solid substrate. The amount of Eag2 bound to the antibody may be determined either by measuring the amount of Eag2 present in a Eag2/antibody complex, or alternatively by measuring the amount of remaining uncomplexed protein. The amount of Eag2 may be detected by providing a labeled Eag2 molecule.

A hapten inhibition assay is another preferred competitive assay. In this assay the known Eag2 is immobilized on a solid substrate. A known amount of anti-Eag2 antibody is added to the sample, and the sample is then contacted with the immobilized Eag2. The amount of anti- Eag2 antibody bound to the known immobilized Eag2 is inversely proportional to the amount of Eag2 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations for Eag2. For example, a protein at least partially encoded by SEQ ID NO:2 or an immunogenic region thereof, such as the C-terminal region (amino acids 720–988), can be immobilized to a solid support. Other proteins such as other Eag subfamily members such as any mammalian Eag1, e.g., human Eag1, or Eag2 orthologs, are added to the assay so as to compete for binding of the antisera to the immobilized antigen. The ability of the added proteins to compete for binding of the antisera to the immobilized protein is compared to the ability of the hEag2 encoded by SEQ ID NO:2 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of Eag2, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by Eag2 that is required to inhibit 50% of binding, then the second protein is said to specifically bind to the polyclonal antibodies generated to the respective Eag2 immunogen.

Other Assay Formats

Western blot (immunoblot) analysis is used to detect and quantify the presence of the Eag2 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind Eag2. The anti-Eag2 antibodies specifically bind to Eag2 on the solid support. These antibodies may be directly labeled or alternatively may be subsequently detected using labeled antibodies (e.g., labeled sheep anti-mouse antibodies) that specifically bind to the anti-Eag2 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize Eag2, or secondary antibodies that recognize anti-Eag2 antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulation of Eag2

A. Assays

Eag2 monomers and Eag2 alleles and polymorphic variants are subunits of potassium channels. The activity of a potassium channel comprising Eag2 can be assessed using a variety of in vitro and in vivo assays, e.g., measuring current, measuring membrane potential, measuring ion flux, e.g., potassium or rubidium, measuring ligand binding, measuring potassium concentration, measuring second messengers and transcription levels, using potassium-dependent yeast growth assays, and using e.g., voltage-sensitive dyes, radioactive tracers, and patch-clamp electrophysiology.

Furthermore, such assays can be used to test for inhibitors and activators of channels comprising Eag2. Such modulators of a potassium channel are useful for treating various disorders involving potassium channels. Treatment of dysfunctions include, e.g., CNS disorders such as migraines, hearing and vision problems, Alzheimer's disease, learning and memory disorders, Alzheimer's disease, learning and memory disorders, seizures, psychotic disorders, and use as neuroprotective agents (e.g., to prevent stroke). Such modulators are also useful for investigation of the channel diversity provided by Eag2 and the regulation/modulation of potassium channel activity provided by Eag2.

Modulators of the potassium channels are tested using biologically active Eag2, either recombinant or naturally occurring. Human Eag2 can be isolated, co-expressed or expressed in a cell, or expressed in a membrane derived from a cell. In such assays, Eag2 is expressed alone to form a homomeric potassium channel or is co-expressed with a second alpha subunit (e.g., another Eag family member, preferably an Eag subfamily member) so as to form a heteromeric potassium channel. Eag2 can also be expressed with additional beta subunits. Modulation is tested using one of the in vitro or in vivo assays described above. Samples or assays that are treated with a potential potassium channel inhibitor or activator are compared to control samples without the test compound, to examine the extent of modulation. Control samples (untreated with activators or inhibitors) are assigned a relative potassium channel activity value of 100. Inhibition of channels comprising Eag2 is achieved when the potassium channel activity value relative to the control is about 90%, preferably 50%, more preferably 25%. Activation of channels comprising Eag2 is achieved when the potassium channel activity value relative to the control is 110%, more preferably 150%, more preferable 200% higher. Compounds that increase the flux of ions will cause a detectable increase in the ion current density by increasing the probability of a channel comprising Eag2 being open, by decreasing the probability of it being closed, by increasing conductance through the channel, and/or by allowing the passage of ions.

Changes in ion flux may be assessed by determining changes in polarization (i.e., electrical potential) of the cell or membrane expressing the potassium channel comprising Eag2. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include: radiolabeled rubidium flux assays and fluorescence assays using ion-sensitive dyes, voltage-sensitive dyes (see, e.g., Vestergarrd-Bogind et al., *J. Membrane Biol.* 88:67–75 (1988); Daniel et al., *J. Pharmacol. Meth.* 25:185–193 (1991); Holevinsky et al., *J. Membrane Biology* 137:59–70 (1994)). Assays for compounds capable of inhibiting or increasing potassium flux through the channel proteins comprising Eag2 can be performed by application of the compounds to a bath solution in contact with and comprising cells having a channel of the present invention (see, e.g., Blatz et al., *Nature* 323:718–720 (1986); Park, *J. Physiol.* 481:555–570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The cations can be measured in a variety of standard ways. They can be measured directly by concentration changes of the ions or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $Ca^{2+}$, or cyclic nucleotides.

Preferably, the Eag2 that is a part of the potassium channel used in the assay will have at least 85% identity to the amino acid sequence displayed in SEQ ID NO:2 or a conservatively modified variant thereof. Alternatively, the Eag2 of the assay will be derived from a eukaryote and include an amino acid subsequence having substantial amino acid sequence identity to the C-terminal region of hEag2. Generally, the amino acid sequence identity will be at least 70%, preferably at least 75, 80, 85 or 90%, most preferably at least 95%.

Human Eag2 orthologs will generally confer substantially similar properties on a channel comprising such Eag2, as described above. In a preferred embodiment, the cell placed in contact with a compound that is suspected to be a Eag2 homolog is assayed for increasing or decreasing ion flux in a eukaryotic cell, e.g., an oocyte of Xenopus (e.g., *Xenopus laevis*) or a mammalian cell such as a CHO or HeLa cell. Channels that are affected by compounds in ways similar to hEag2 are considered homologs or orthologs of hEag2.

B. Modulators

The compounds tested as modulators of Eag2 channels comprising a human Eag2 subunit can be any small chemical compound, or a biological entity, such as a protein, sugar, nucleic acid or lipid. Alternatively, modulators can be genetically altered versions of a human Eag2 subunit. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chem et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. Nos. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using potassium channels comprising an Eag2 polypeptide, e.g., hEag2; a membrane comprising an Eag2 potassium channel, or a cell or tissue expressing potassium channels comprising a Eag2 polypeptide, either naturally occurring or recombinant. In another embodiment, the invention provides solid phase based in vitro assays in a high throughput format, where Eag2 potassium channel, or a cell or cell membrane expressing an Eag2 potassium channel, is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

The channel of interest, or a cell or membrane comprising the channel of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearnvater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

VII. Computer Assisted Drug Design Using Eag2

Yet another assay for compounds that modulate the activities of Eag2 involves computer assisted drug design, in which a computer system is used to generate a three-dimensional structure of Eag2 based on the structural information encoded by the amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind, e.g., ligands or other potassium channel subunits. These regions are then used to identify ligands that bind to the protein or region where Eag2 interacts with other potassium channel subunits. The three-dimensional structural model of the protein is generated by entering channel protein amino acid sequences of at least 50, preferably 75, 100, or 150 amino acid residues or corresponding nucleic acid sequences encoding an Eag2 monomer into the computer system. The amino acid sequence of each of the monomers is selected from the group consisting of SEQ ID NO:2 and a conservatively modified versions thereof. The amino acid sequence represents the primary sequence or subsequence of each of the proteins, which encodes the structural information of the protein. At least 50, preferably 75, 100, or 150 residues of the amino acid sequence (or a nucleotide sequence encoding at least 50, preferably 75, 100, or 150 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the channel protein is then generated by the interaction of the amino acid sequence and the computer system, using software known to those of skill in the art. The resulting three-dimensional computer model can then be saved on a computer readable substrate.

The amino acid sequence represents a primary structure that encodes the information necessary to form the secondary, tertiary and quaternary structure of the monomer and the heteromeric potassium channel protein comprising four monomers. The software looks at certain parameters encoded by the primary sequence to generate the structural model. These parameters are referred to as "energy terms," or anisotropic terms and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of Eag2 protein to identify ligands that bind to Eag2. Binding affinity between the protein and ligands is determined using energy terms to determine which ligands have an enhanced probability of binding to the protein.

Computer systems are also used to screen for mutations, polymorphic variants, alleles, and interspecies homologs of Eag2 genes. Such mutations can be associated with disease states. Once the variants are identified, diagnostic assays can be used to identify patients having such mutated genes associated with disease states. Identification of the mutated Eag2 genes involves receiving input of a first nucleic acid, e.g., SEQ ID NO:1, or an amino acid sequence encoding Eag2, selected from the group consisting of SEQ ID NO:2, and a conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in Eag2 genes, and mutations associated with disease states. The first and second sequences described above can be saved on a computer readable substrate.

Human Eag2 monomers and the potassium channels containing these Eag2 monomers can be used with high density oligonucleotide array technology (e.g., GeneChip™) to identify homologs and polymorphic variants of Eag2 in this invention. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

VIII. Cellular Transfection and Gene Therapy

The present invention provides the nucleic acids of Eag2 for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid for Eag2, under the control of a promoter, then expresses a Eag2 monomer of the present invention, thereby mitigating the effects of absent, partial inactivation, or abnormal expression of the Eag2 gene.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, *TIBTECH* 11:211–217 (1993); Mitani & Caskey, *TIBTECH* 11:162–166 (1993); Mulligan, *Science* 926–932 (1993); Dillon, *TIBTECH* 11:167–175 (1993); Miller, *Nature* 357:455–460 (1992); Van Brunt, *Biotechnology* 6(10):1149–1154 (1998); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfler & Böhm eds., 1995); and Yu et al., *Gene Therapy* 1:13–26 (1994)).

Delivery of the gene or genetic material into the cell is the first critical step in gene therapy treatment of disease. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell.

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404–410 (1995); Blaese et al., *Cancer Gene Ther.* 2:291–297 (1995); Behr et al., *Bioconjugate Chem.* 5:382–389 (1994); Remy et al., *Bioconjugate Chem.* 5:647–654 (1994); Gao et al., *Gene Therapy* 2:710–722 (1995); Ahmad et al., *Cancer Res.* 52:4817–4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuL V), gibbon ape leukemia virus (GaL V), simian immunodeficiency virus (SIV), human immunodeficiency virus (HIV), and combinations thereof (see, e.g., Buchscher et al., *J. Virol.* 66:2731–2739 (1992); Johann et al., *J. Virol.* 66:1635–1640 (1992); Sommerfelt et al., *Virol.* 176:58–59 (1990); Wilson et al., *J. Virol.* 63:2374–2378 (1989); Miller et al., *J. Virol.* 65:2220–2224 (1991); PCT/US94/05700).

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38–47 (1987); U.S. Pat. No. 4,797,368; WO 93/24641; Kotin, *Human Gene Therapy* 5:793–801 (1994); Muzyczka, *J. Clin. Invest.* 94:1351 (1994)). Construction of recombinant AAV vectors are described in a number of publications, including U.S. Pat. No. 5,173,414; Tratschin et al., *Mol. Cell. Biol.* 5:3251–3260 (1985); Tratschin et al., *Mol. Cell. Biol.* 4:2072–2081 (1984); Hermonat & Muzyczka, *Proc. Natl. Acad. Sci. U.S.A.* 81:6466–6470 (1984); and Samulski et al., *J. Virol.* 63:03822–3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048–305 (1995); Kohn et al., *Nat. Med.* 1:1017–102 (1995); Malech et al., *Proc. Natl. Acad. Sci. U.S.A.* 94:22 12133–12138 (1997)). PA317/pLASN was the first therapeutic vector used in a gene therapy trial. (Blaese et al., *Science* 270:475–480 (1995)). Transduction efficiencies of 50% or greater have been observed for MFG-S packaged vectors (Ellem et al., *Immunol Immunother.* 44(1):10–20 (1997); Dranoff et al., *Hum. Gene Ther.* 1:111–2 (1997)).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system (Wagner et al., *Lancet* 351:9117 1702–3 (1998), Kearns et al., *Gene Ther.* 9:748–55 (1996)).

Replication-deficient recombinant adenoviral vectors (Ad) are predominantly used transient expression gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083–9 (1998)). Additional examples of the use of adenovirus vectors for gene transfer in clinical trials include Rosenecker et al., *Infection* 241:5–10 (1996); Sterman et al., *Hum. Gene Ther.* 9:7 1083–1089 (1998); Welsh et al., *Hum. Gene Ther.* 2:205–18 (1995); Alvarez et al., *Hum. Gene Ther.* 5:597–613 (1997); Topf et al., *Gene Ther.* 5:507–513 (1998); Sterman et al., *Hum. Gene Ther.* 7:1083–1089 (1998).

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Natl. Acad. Sci. U.S.A.* 92:9747–9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Administration is by any of the routes normally used for introducing a molecule into ultimate contact with blood or tissue cells. The nucleic acids are administered in any suitable manner, preferably with pharmaceutically acceptable carriers. Suitable methods of administering such nucleic acids are available and well known to those of skill in the art, and, although more than one route can be used to administer a particular composition, a particular route can often provide a more immediate and more effective reaction than another route.

IX. Pharmaceutical Compositions

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989).

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial response in the subject over time. Such doses are administered prophylactically or to an individual already suffering from the disease. The compositions are administered to a patient in an amount sufficient to elicit an effective protective or therapeutic response in the patient. An amount adequate to accomplish this is defined as "therapeutically effective dose." The dose will be determined by the efficacy of the particular Eag2 modulators (e.g., Eag2 antagonists and anti-Eag2 antibodies) employed and the condition of the subject, as well as the body weight or surface area of the area to be treated. The size of the dose also will be determined by the existence, nature, and extent of any adverse side-effects that accompany the administration of a particular compound or vector in a particular subject.

In determining the effective amount of the compound to be administered in the treatment or prophylaxis of conditions owing to diminished or aberrant expression of the Eag2 channels comprising a human Eag2 alpha subunit, the physician evaluates circulating plasma levels of the compound, compound toxicities, progression of the disease, and the production of antibodies. In general, the dose equivalent of a compound is from about 1 $\mu$g to 100 $\mu$g for a typical 70 kilogram patient.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

Transduced cells are prepared for reinfusion according to established methods (see, e.g., Abrahamsen et al., *J. Clin. Apheresis* 6:48–53 (1991); Carter et al., *J. Clin. Apheresis* 4:113–117 (1998); Aebersold et al., *J. Immunol. Meth.* 112:1–7 (1998); Muul et al., *J. Immunol. Methods* 101: 171–181 (1987); and Carter et al., *Transfusion* 27:362–365 (1987)).

X. Kits

Human Eag2 and its homologs are useful tools for examining expression and regulation of potassium channels. Human Eag2-specific reagents that specifically hybridize to Eag2 nucleic acid, such as Eag2 probes and primers, and Eag2-specific reagents that specifically bind to the Eag2 protein, e.g., Eag2 antibodies are used to examine expression and regulation.

Nucleic acid assays for the presence of Eag2 DNA and RNA in a sample include numerous techniques are known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987). In addition, Eag2 protein can be detected with the various immunoassay techniques described above. The test sample is typically compared to both a positive control (e.g., a sample expressing recombinant Eag2 monomers) and a negative control.

The present invention also provides for kits for screening modulators of the heteromeric potassium channels. Such kits can be prepared from readily available materials and reagents. For example, such kits can comprise any one or more of the following materials: Eag2 monomers, reaction tubes, and instructions for testing the activities of potassium channels containing Eag2. A wide variety of kits and components can be prepared according to the present invention, depending upon the intended user of the kit and the particular needs of the user. For example, the kit can be tailored for in vitro or in vivo assays for measuring the activity of a potassium channel comprising a Eag2 monomer.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following example is provided by way of illustration only and not by way of limitation. Those of skill in the art will readily recognize a variety of noncritical parameters that could be changed or modified to yield essentially similar results.

Example I

Cloning and Expression of hEAG2

Using PCR and primers, according to standard conditions, hEag2 was amplified from human brain tissue cDNA, e.g., whole brain or hippocampus cDNA. The following primers were used for amplification:

ATGCCGGGGGGCAAGAGAGGGCTG (SEQ ID NO:3);

CTGACCCTAAGCTCATAAGGATGAAC (SEQ ID NO:4);

CCACCTCATCATCCTGGATGACTTCC (SEQ ID NO:5);

TTAAAAGTGGATTTCATCTTTGTCAGATTCAGG (SEQ ID NO:6);

GGGGACCTCATTTACCATGCTGGAG (SEQ ID NO:7)

GATTCCCTCATCCACATTTTCAAAGGC (SEQ ID NO:8).

The SEQ ID NO:3 and 6 oligos also include additional adaptor sequences used for expression vector construction (enzyme sites, Kozak consensus) that are not present in Eag2 (additional adaptor sequences not shown). SEQ ID NO:7 can be used with SEQ ID NO:6 to amplify a region of Eag2 extending from the putative cyclic nucleotide binding domain through the stop codon. SEQ ID NO:8 can be used with SEQ ID NO:3 to amplify a region extending from the initiator methionine to the S4 domain. SEQ ID NOS:3 and 6 were used to amplify the entire coding region. SEQ ID NOS:4 and 5 can be used to amplify an approximately 950 bp fragment from just upstream of S3 to the putative cyclic nucleotide binding domain. SEQ ID NOS:3 and 5 can be used to amplify from the initiator methionine to the cyclic-nucleotide binding domain (the sequence encoding approximately amino acids 1–720), and SEQ ID NOS:4 and 6 can be used to amplify from S3 to the stop codon. At least one of these primers should amplify all splice variants. The cDNA was prepared from total mRNA isolated from human brain tissue, e.g., whole brain or hippocampus, according to standard methods. hEag2 was amplified with the primers described above using the following conditions: 30 seconds at 95° C., 15 seconds at 68–58° C., and 3 minutes at 72° C. for 40 cycles.

The PCR products were subcloned into plasmids and sequenced according to standard techniques. The nucleotide and amino acid sequences of hEag2 are provided, respectively, in SEQ ID NO:1 and SEQ ID NO:2 (see also FIG. 1).

mRNA distribution of hEag2 was examined according to standard techniques. In a northern blot, the Eag2 probe recognized an approximately 12 kb transcript in the brain, and also fainter 8 and 4.5 kb transcripts in the brain. In a dot blot, Eag2 expression was the highest in the occipital lobe, thalamus, temporal lobe, nucleus accumbens and pituitary gland. Expression was also detected in frontal lobe, hippocampus, cerebral cortex, medulla, adrenal gland, and testis.

Example II

Expression and Voltage-gated Activity of Homomeric Channels Containing hEag2 Monomers hEag2 monomer was expressed in both Xenopus oocytes and CHO cells according to standard methodology, to demonstrate its ability to form homomeric potassium channels with voltage-gated activity. Changes in current magnitude can be indirectly measured using a reporter voltage-sensitive fluorescent dye (see, e.g., Etts et al., *Chemistry and Physiology of Lipids*, 69:137 (1994)). Changes in current magnitude can also be measured directly using electrophysiology, and by measuring ion flux.

hEag2 channels are potassium selective and voltage-sensitive. When Eag2 was functionally expressed in either *Xenopus oocytes* or mammalian cells, it produced an outwardly rectifying potassium current with relatively weak voltage-dependence (see FIGS. 2 and 3). Activation of the Eag2 current begins at subthreshold potentials, with the midpoint of the activation curve lying between approximately –30 and –20 mV. There is no evidence of inactivation. These properties potentially give the Eag2 current a role in contributing to cellular resting potentials and influencing excitability in both the subthreshold and suprathreshold voltage ranges (that means that the Eag2 current could influence the whether or not a neuron fires and action potential and/or the shape of that action potential). The activation rate of Eag2 is very sensitive to holding potential. If a depolarization occurs from a very hyperpolarized potential, Eag2 activation is very slow, occurring over several seconds. However, activation potentials close to typical cell resting potentials (–80 to –50 mV) is very rapid, allowing the Eag2 outward current to counteract the depolarization quickly.

What is claimed is:

1. An isolated nucleic acid encoding a polypeptide comprising an alpha subunit of a potassium channel, wherein the subunit:
   (i) forms, with at least one additional Eag family alpha subunit, a potassium channel having the characteristic of voltage sensitivity; and wherein said nucleic acid specifically hybridizes under stringent conditions to SEQ ID NO:1, wherein the hybridization reaction is incubated at 42° C. in a solution comprising 50% formamide, 5×SSC, and 1% SDS or at 65° C. in a solution comprising 5×SSC and 1% SDS, with a wash in 0.2×SSC and 0.1% SDS at 65° C.

2. An isolated nucleic acid encoding a polypeptide comprising an alpha subunit of a potassium channel, wherein the subunit:
   (i) forms, with at least one additional Eag family alpha subunit, a potassium channel having the characteristic of voltage sensitivity; and
   (ii) comprises an amino acid sequence that has greater than 85% amino acid identity to the amino acid sequence of SEQ ID NO:2.

3. The isolated nucleic acid of claim 1, wherein the polypeptide specifically binds to polyclonal antibodies generated against SEQ ID NO:2.

4. The isolated nucleic acid of claim 1, wherein the nucleic acid encodes human Eag2.

5. The isolated acid of claim 1, wherein the nucleic acid encodes an amino acid sequence of SEQ ID NO:2.

6. The isolated nucleic acid sequence of claim 1, wherein the nucleic acid has a nucleotide sequence of SEQ ID NO:1.

7. The isolated nucleic acid of claim 1, wherein the nucleic acid is amplified by primers that selectively hybridize under stringent hybridization conditions to the same sequence as primers selected from the group consisting of:

ATGCCGGGGGGCAAGAGAGGGCTG (SEQ ID NO:3);

CTGACCCTAAGCTCATAAGGATGAAC (SEQ ID NO:4);

CCACCTCATCATCCTGGATGACTTCC (SEQ ID NO:5);

TTAAAAGTGGATTTCATCTTTGTCAGATTCAGG (SEQ ID NO :6);

GGGGACCTCATTTACCATGCTGGAG (SEQ ID NO:7);

GATTCCCTCATCCACATTTTCAAAGGC (SEQ ID NO:8);

and wherein the hybridization reaction is incubated at 42° C. in a solution comprising 50% formamide, 5×SSC, and 1% SDS or at 65° C. in a solution comprising 5×SSC and 1% SDS, with a wash in 0.2×SSC and 0.1% SDS at 65° C.

8. The isolated nucleic acid of claim 1, wherein the polypeptide monomer comprises an alpha subunit of a homomeric channel.

9. The isolated nucleic acid of claim 1, wherein the polypeptide monomer comprises an alpha subunit of a heteromeric channel.

10. An expression vector comprising the nucleic acid of claim 1.

11. A host cell transfected with the vector of claim 10.

12. A method of detecting a nucleic acid, the method comprising contacting a sample comprising a first nucleic acid with an isolated second nucleic acid of claim 1 and detecting hybridization of the second nucleic acid to the first nucleic acid, thereby detecting the first nucleic acid.

* * * * *